US010220070B2

(12) United States Patent
Fort et al.

(10) Patent No.: US 10,220,070 B2
(45) Date of Patent: Mar. 5, 2019

(54) ALPHAA-CRYSTALLIN MIMETIC PEPTIDES AND USES THEREOF

(71) Applicants: The Regents of the University of Michigan, Ann Arbor, MI (US); Vanderbilt University, Nashville, TN (US)

(72) Inventors: Patrice E. Fort, Ann Arbor, MI (US); Kevin Schey, Nashville, TN (US)

(73) Assignees: The Regents of the University of Michigan, Ann Arbor, MI (US); Vanderbilt University, Nashville, TN (US)

( * ) Notice: Subject to any disclaimer, the term of this patent is extended or adjusted under 35 U.S.C. 154(b) by 0 days.

(21) Appl. No.: 15/707,596

(22) Filed: Sep. 18, 2017

(65) Prior Publication Data

US 2018/0078607 A1 Mar. 22, 2018

Related U.S. Application Data

(60) Provisional application No. 62/397,199, filed on Sep. 20, 2016.

(51) Int. Cl.
| | | |
|---|---|---|
| A61K 38/16 | (2006.01) | |
| C07K 4/00 | (2006.01) | |
| A61K 31/57 | (2006.01) | |
| A61K 9/00 | (2006.01) | |

(52) U.S. Cl.
CPC ............... A61K 38/16 (2013.01); C07K 4/00 (2013.01); *A61K 9/0048* (2013.01); *A61K 31/57* (2013.01)

(58) Field of Classification Search
None
See application file for complete search history.

(56) References Cited

PUBLICATIONS

Abcouwer SF, et al. Vascular Permeability and Apoptosis are Separable Processes in Retinal Ischemia-Reperfusion Injury: Effects of Ischemic Preconditioning, Bevacizumab and Etanercept. Invest Ophthalmol Vis Sci. 2010, vol. 51, 5920-5933., Epub Jun. 18, 2010.
Amoaku WM, Saker S. et al., A review of therapies for diabetic macular oedema and rationale for combination therapy. Eye (London, England). 2015;29(9):1115-30.
Antonetti DA, et al., Vascular permeability in experimental diabetes is associated with reduced endothelial occludin content: vascular endothelial growth factor decreases occludin in retinal endothelial cells. Penn State Retina Research Group Diabetes. 1998;47(12)1953-9.
Arac A, et al., "Systemic augmentation of alphaB-crystallin provides therapeutic benefit twelve hours post-stroke onset via immune modulation." Proc Natl Acad Sci U S A. 2011;108(32):13287-92.

Barber AJ, et al., "Altered expression of retinal occludin and glial fibrillary acidic protein in experimental diabetes. The Penn State Retina Research Group." Invest Ophthalmol Vis Sci. 2000;41(11):3561-8.
Barber AJ, et al., "The Ins2Akita mouse as a model of early retinal complications in diabetes." Invest Ophthalmol Vis Sci. 2005;46(6):2210-8.
Barber AJ, et al., Neural apoptosis in the retina during experimental and human diabetes. Early onset and effect of Insulin. J Clin Invest. 1998;102(4):783-91.
Brady JP, et al., AlphaB-crystallin in lens development and muscle integrity: a gene knockout approach. Invest Ophthalmol Vis Sci. 2001;42(12):2924-34.
Brady JP, et al., Targeted disruption of the mouse alpha A-crystallin gene induces cataract and cytoplasmic inclusion bodies containing the small heat shock protein alpha B-crystallin. Proc Natl Acad Sci U S A. 1997;94(3):884-9.
Brownell SE, et al., The protective and therapeutic function of small heat shock proteins in neurological diseases. Frontiers in immunology. 2012;3:74 1-10.
Dong Z, et al. Alphab-Crystallin Expression in Epiretinal Membrane of Human Proliferative Diabetic Retinopathy. Retina. Jun. 2012;32(6):1190-6.
Fort PE, et al., The retinal proteome in experimental diabetic retinopathy: up-regulation of crystallins and reversal by systemic and periocular insulin. Mol Cell Proteomics. 2009;8(4):767-79.
Heise EA, et al. Strain-independent increases of crystallin proteins in the retina of type 1 diabetic rats. PLoS One. 2013;8(12):e82520.
Kase S, et al., alphaB-crystallin regulation of angiogenesis by modulation of VEGF. Blood. 2010;115(16):3398-406.
Kase S, et al. Increased expression of alphaA-crystallin in human diabetic eye. Int J Mol Med. 2011;28(4):505-11.
Klein R, Klein BEK. The Prevalence of Age-Related Eye Diseases and Visual Impairment in Aging: Current Estimates Investigative ophthalmology & visual science. 2013;54(14).
Kumar PA, et al., Elevated expression of alphaA- and alphaB-crystallins in streptozotocin-induced diabetic rat. Arch Biochem Biophys. 2005;444(2):77-83.
Liu JP, et al., Human alphaA- and alphaB-crystallins prevent UVA-induced apoptosis through regulation of PKCalpha, RAF/MEK/ERK and AKT signaling pathways. Exp Eye Res. 2004;79(3):393-403.
Losiewicz MK, et al., Diabetes impairs the neuroprotective properties of retinal alpha-crystallins. Invest Ophthalmol Vis Sci. 2011;52(9):5034-42.
Maclean B, et al., Skyline: an open source document editor for creating and analyzing targeted proteomics experiments. Bioinformatics. 2010;26(7):966-8.
Martin PM, et al., Death of retinal neurons in streptozotocin-induced diabetic mice. Invest Ophthalmol Vis Sci. 2004;45(9):3330-6.

(Continued)

*Primary Examiner* — Fred H Reynolds
(74) *Attorney, Agent, or Firm* — Casimir Jones, SC; Robert A. Goetz

(57) ABSTRACT

This invention relates to αA-crystallin protein modulating compounds (e.g., phosphomimetic peptides), compositions comprising such modulating compounds, and their use as therapeutics for the treatment and prevention of conditions involving neurodegeneration and neuroinflammation.

2 Claims, 14 Drawing Sheets

Specification includes a Sequence Listing.

(56) References Cited

PUBLICATIONS

Rao NA, et al., Elevated retina-specific expression of the small heat shock protein, alphaA-crystallin, is associated with photoreceptor protection in experimental uveitis. Invest Ophthalmol Vis Sci. 2008;49(3):1161-71.

Rao NA, et al., Small Heat Shock Protein αA-Crystallin Prevents Photoreceptor Degeneration in Experimental Autoimmune Uveitis PLoS One. 2012;7(3) e35582; 1-8.

Reiter CE, et al., Characterization of insulin signaling in rat retina in vivo and ex vivo. Am J Physiol Endocrinol Metab. 2003;285(4):E763-74.

Reiter CE, et al., Diabetes reduces basal retinal insulin receptor signaling: reversal with systemic and local insulin. Diabetes. 2006;55(4):1148-56.

Schmidt T, et al., Induction and phosphorylation of the small heat shock proteins HspB1/Hsp25 and HspB5/αB-arystallin in the rat retina upon optic nerve injury. Cell stress & chaperones. 2016;21(1):167-78.

Sinha D, et al., βA3/A1-crystallin in astroglial cells regulates retinal vascular remodeling during development. Mol Cell Neurosci. 2008;37(1):85-95.

Sohn EH, et al., Retinal neurodegeneration may precede microvascular changes characteristic of diabetic retinopathy in diabetes mellitus. Proc Natl Acad Sci U S A. 2016;113(19) E2655-64.

Thompson DA, et al., Retinal on-pathway deficit in congenital disorder of glycosylation due to phosphomannomutase leficiency. Arch Ophthalmol. 2012;130(6):712-9.

Nhiston EA, et al., alphaB-crystallin protects retinal tissue during Staphylococcus aureus-induced endophthalmitis. Infect Immun. 2008;76(4):1781-90.

Wu X, et al., Insulin promotes rat retinal neuronal cell survival in a p70S6K-dependent manner. J Biol Chem. 2004;279 (10):9167-75.

Yaung J, et al., Exacerbation of retinal degeneration in the absence of alpha crystallins in an in vivo model of ahemically induced hypoxia. Exp Eye Res. 2008;86(2):355-65.

Zeng XX, et al., Neuronal and microglial response in the retina of streptozotocin-induced diabetic rats. Vis Neurosci. 2000;17(3):463-71.

FIG. 4A
FIG. 4C
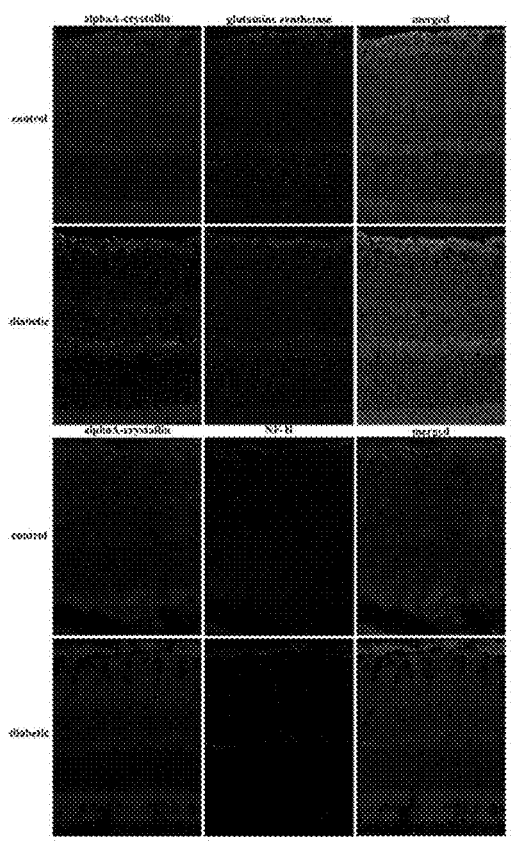
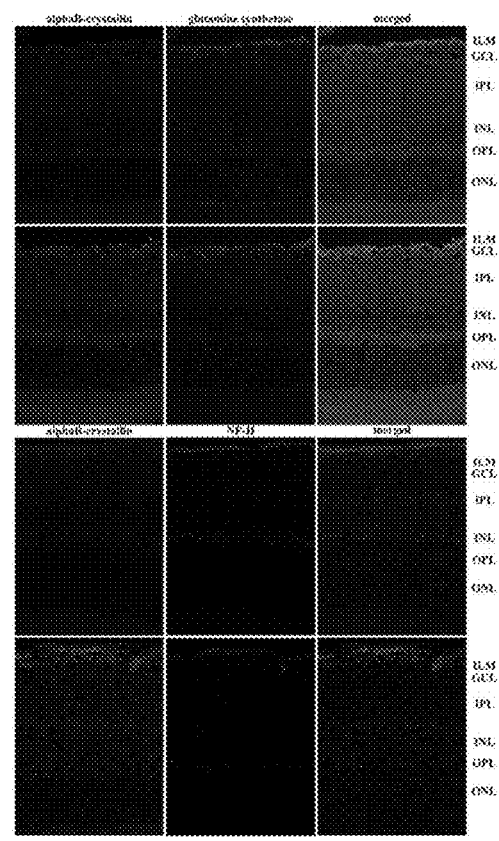
FIG. 4B
FIG. 4D

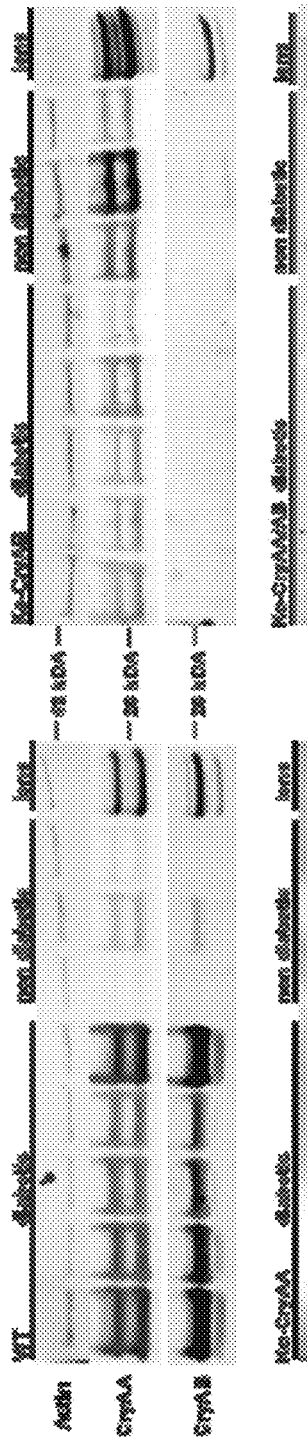
FIG. 5A
FIG. 5B
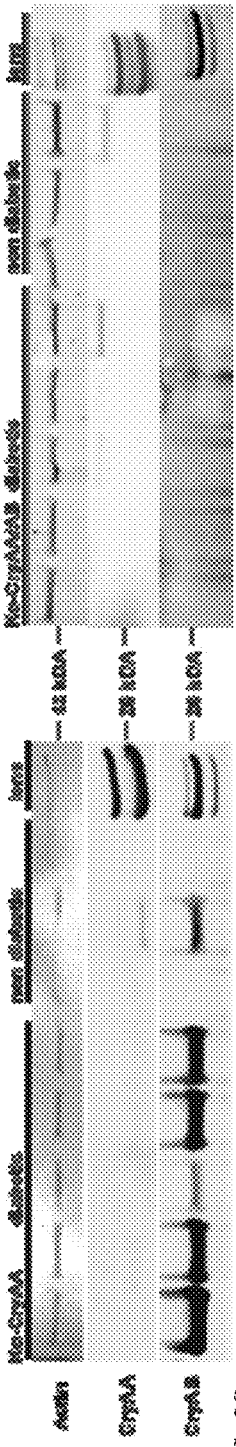
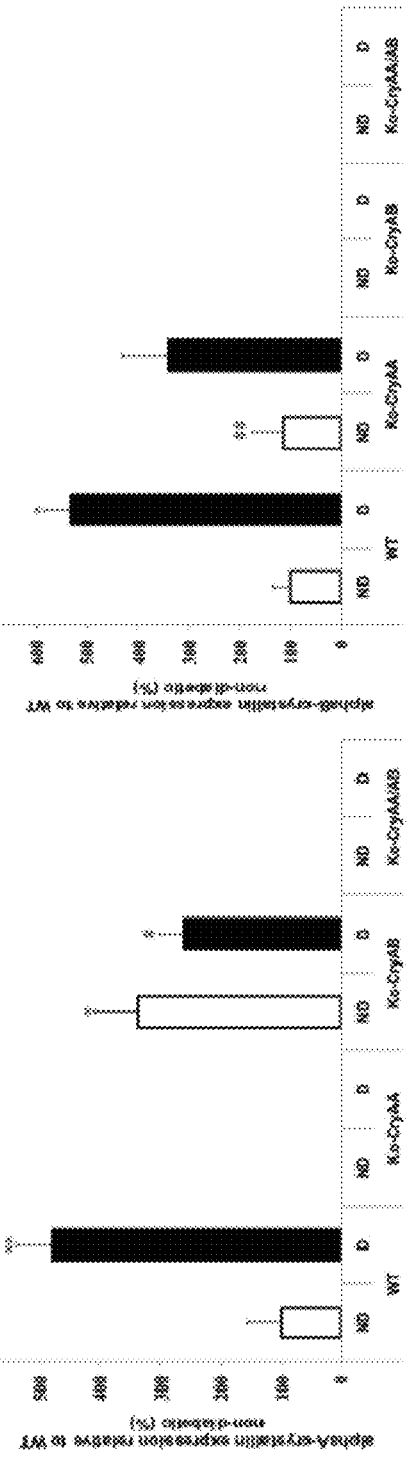
FIG. 5C
FIG. 5D

FIG. 8

```
aA-mouse      MDVTIQHPWFKRALGPFYPSRLFDQFFGEGLFEYDLLPFLSSTISPYYRQSLFRTVLDSG  60
aA-human      MDVTIQHPWFKRTLGPFYPSRLFDQFFGEGLFEYDLLPFLSSTISPYYRQSLFRTVLDSG  60
              **********:********************************************* aA-mouse      ISEVRSDRDKFVIFLDVKHFSPEDLTVKVLEDFVEIHGKHNERQDDHGYISREFHRRYRL  120
aA-human      ISEVRSDRDKFVIFLDVKHFSPEDLTVKVQDDFVEIHGKHNERQDDHGYISREFHRRYRL  120
              ***************************  :************************* aA-mouse      PSNVDQSALSCSLSADGMLTFSGPKVQSGLDAGHSERAIPVSREEKPSSAPSS  173
aA-human      PSNVDQSALSCSLSADGMLTFCGPKIQTGLDATHAERAIPVSREEKPTSAPSS  173
```

ALPHAA-CRYSTALLIN MIMETIC PEPTIDES AND USES THEREOF

STATEMENT REGARDING FEDERALLY SPONSORED RESEARCH OR DEVELOPMENT

This invention was made with government support under EY020895 awarded by the National Institutes of Health. The government has certain rights in the invention.

FIELD OF THE INVENTION

This invention relates to αA-crystallin protein modulating compounds (e.g., phosphomimetic peptides), compositions comprising such modulating compounds, and their use as therapeutics for the treatment and prevention of conditions involving neurodegeneration and neuroinflammation.

INTRODUCTION

Diabetes mellitus (DM) is a major medical problem throughout the world. Diabetes causes an array of long-term systemic complications that have considerable impact on the patient as well as society, as the disease typically affects individuals in their most productive years (see, Federman J L, Gouras P, Schubert H, et al. Systemic diseases. Podos S M, Yanoff M, eds. *Retina and Vitreous: Textbook of Ophthalmology.* 1994. Vol 9: 7-24). An increasing prevalence of diabetes is occurring throughout the world (see, Bhaysar A R, Emerson G G, Emerson M V, Browning D J. Diabetic Retinopathy. Browning D J. *Epidemiology of Diabetic Retinopathy*. Springer, New York: 2010). In addition, this increase appears to be greater in developing countries. The etiology of this increase involves changes in diet, with higher fat intake, sedentary lifestyle changes, and decreased physical activity (see, Williams R, et al., Eye (Lond). 2004 Oct. 18(10):963-83; Gupta R, Kumar P. Insulin; 2008. 3:78-94).

Patients with diabetes often develop ophthalmic complications, such as corneal abnormalities, glaucoma, iris neovascularization, cataracts, and neuropathies. The most common and potentially most blinding of these complications, however, is diabetic retinopathy (see, Cai X, McGinnis J F. J Diabetes Res. 2016. 2016:3789217; Aiello L M, Cavallerano J D, Aiello L P, Bursell S E. Diabetic retinopathy. Guyer D R, Yannuzzi L A, Chang S, et al, eds. *Retina Vitreous Macula.* 1999. Vol 2: 316-44; Benson W E, Tasman W, Duane T D. Diabetes mellitus and the eye. *Duane's Clinical Ophthalmology.* 1994. Vol 3), which is, in fact, the leading cause of new blindness in persons aged 25-74 years in the United States. Approximately 700,000 persons in the United States have proliferative diabetic retinopathy, with an annual incidence of 65,000. An estimate of the prevalence of diabetic retinopathy in the United States showed a high prevalence of 28.5% among those with diabetes aged 40 years or older (see, Zhang X, et al., JAMA. 2010 Aug. 11. 304(6):649-56).

Improved methods for understanding, preventing and/or treating diabetic retinopathy are needed.

SUMMARY OF THE INVENTION

Diabetes and its complications are major health considerations worldwide and expected to increase in the next few decades. It has been previously demonstrated that alpha-crystallins are highly upregulated in the retina of diabetic rodents, and that their upregulation in retinal neurons is associated with an increased survival in response to metabolic and inflammatory stresses; however their exact function in the retina, and their regulation during diabetes remained unclear.

The present invention resolves this ambiguity. Indeed, experiments conducted during the course of developing embodiments for the present invention used a combination of genetic and phenotypic analysis to explore the basic regulation and function of αA- and αB-crystallin in the retina in the context of diabetes. A time-dependent analysis revealed that lack of αA-crystallin leads to rapidly increased cell death and decreased retinal function following diabetes induction, while lack of αB-crystallin caused functional perturbation without detectable cellular loss. Further, lack of αB-crystallin can be compensated by increased levels of αA-crystallin but not vice-versa suggesting a more fundamental role for αA-crystallin in the retina. It was also shown that the protective function of αA-crystallin is associated with regulation of the function of the pro-apoptotic protein Bax and that diabetes alters αA-crystallins' function via post-translational modifications, including a novel and key phosphorylation site (human T148 within the human amino acid sequence shown at SEQ ID NO: 1; rodent S148 within the murine amino acid sequence shown at SEQ ID NO: 2). These results support an important role for both alpha-crystallins in retinal function, and demonstrate how αA-crystallin has a central protective function in the retina and how this function can be altered by diabetes.

Accordingly, the present invention relates to αA-crystallin protein modulating compounds (e.g., phosphomimetic peptides), compositions comprising such modulating compounds, and their use as therapeutics for the treatment and prevention of conditions involving neurodegeneration and neuroinflammation.

The invention further relates to methods of treating, ameliorating, or preventing disorders in a subject, such as those that are characterized by aberrant αA-crystallin protein activity (e.g., diabetic retinopathy). In some embodiments, the aberrant αA-crystallin protein activity is the result of post translational modification rendering the protein incapable of phosphorylation at T148 within SEQ ID NO: 1 for human patients and S148 within SEQ ID NO: 2 for rodents. Such methods comprise, for example, administering to the subject (e.g., a human patient) a composition comprising one or more αA-crystallin protein modulating compounds of the invention and, potentially, additional agent(s).

Such methods are not limited to a particular manner of administration. In some embodiments, the composition is administered through direct injection into the subject's ocular region (e.g., eye).

The present invention is not limited to particular types or kinds of αA-crystallin protein modulating compounds. In some embodiments, the αA-crystallin protein modulating compound is a compound configured to mimic wild type αA-crystallin protein activity. In some embodiments, the αA-crystallin protein modulating compound is a compound configured to mimic wild type αA-crystallin protein activity when phosphorylated at amino acid position 148 within SEQ ID NO: 1 for human subjects and SEQ ID NO: 2 for rodents. In some embodiments, the αA-crystallin protein modulating compound is a phosphomimetic peptide having an amino acid sequence having a threonine (T) to aspartic acid (D) substitution at amino acid position 148 within SEQ ID NO: 1. In some embodiments, the αA-crystallin protein modulating compound is a phosphomimetic peptide having an amino acid sequence having a threonine (T) to glutamate (E) substitution at amino acid position 148 within SEQ ID NO:

1. In some embodiments, the αA-crystallin protein modulating compound is a phosphomimetic peptide having an amino acid sequence having a serine (S) to aspartic acid (D) substitution at amino acid position 148 within SEQ ID NO: 2. In some embodiments, the αA-crystallin protein modulating compound is a phosphomimetic peptide having an amino acid sequence having a serine (S) to glutamate (E) substitution at amino acid position 148 within SEQ ID NO: 2. In some embodiments, the αA-crystallin protein modulating compound is a small molecule compound configured to mimic wild type αA-crystallin protein activity phosphorylated at amino acid position 148 within SEQ ID NO: 1 or 2. In some embodiments, the αA-crystallin protein modulating compound is a phosphomimetic peptide having an amino acid sequence comprising a portion (e.g., 50%, 55%, 60%, 65%, 70%, 75%, 80%, 85%, 90%, 95%, 97%, 98%, 99%, 99.5%, 99.8%, 99.9%, 100%) of SEQ ID NO: 1 having a threonine (T) to aspartic acid (D) substitution at amino acid position 148 and retaining wild type activity. In some embodiments, the αA-crystallin protein modulating compound is a phosphomimetic peptide having an amino acid sequence comprising a portion (e.g., 50%, 55%, 60%, 65%, 70%, 75%, 80%, 85%, 90%, 95%, 97%, 98%, 99%, 99.5%, 99.8%, 99.9%, 100%) of SEQ ID NO: 1 having a threonine (T) to glutamate (E) substitution at amino acid position 148 and retaining wild type activity. In some embodiments, the αA-crystallin protein modulating compound is a phosphomimetic peptide having an amino acid sequence comprising a portion (e.g., 50%, 55%, 60%, 65%, 70%, 75%, 80%, 85%, 90%, 95%, 97%, 98%, 99%, 99.5%, 99.8%, 99.9%, 100%) of SEQ ID NO: 2 having a serine (S) to aspartic acid (D) substitution at amino acid position 148 and retaining wild type activity. In some embodiments, the αA-crystallin protein modulating compound is a phosphomimetic peptide having an amino acid sequence comprising a portion (e.g., 50%, 55%, 60%, 65%, 70%, 75%, 80%, 85%, 90%, 95%, 97%, 98%, 99%, 99.5%, 99.8%, 99.9%, 100%) of SEQ ID NO: 2 having a serine (S) to glutamate (E) substitution at amino acid position 148 and retaining wild type activity.

In some embodiments, the αA-crystallin protein modulating compound is any type of moiety (e.g., compound, mimetic, kinases, phosphatases, etc.) capable of a direct or indirect phosphorylation of αA-crystallin.

In some embodiments, the αA-crystallin protein modulating compound is configured to inhibit caspase 3/7 activity. In some embodiments, the αA-crystallin protein modulating compound is configured to inhibit apoptosis effectors such as caspase 3/7, and/or apoptosis regulators such as Bax or Bcl/Xs.

In some embodiments, the methods further comprise administering to the subject one or more additional agents. In some embodiments, the additional agent is a corticosteroid (e.g., triamcinolone), and/or a VEGF inhibitor (e.g., ranibizumab, aflibercept intravitreal).

In certain embodiments, the present invention provides methods for mimicking the activity of αA-crystallin protein phosphorylated at amino acid 148 in a subject (e.g., human subject, non-human subject), comprising administering to the subject a αA-crystallin protein modulating compound as described herein (e.g., a phosphomimetic peptide αA-crystallin protein having a T148D substitution within SEQ ID NO: 1 for human subjects) (e.g., a phosphomimetic peptide αA-crystallin protein having a S148D substitution within SEQ ID NO: 2 for rodent subjects). In some embodiments, the subject has or is at risk for developing diabetic retinopathy.

In some embodiments, the methods further comprise administering to the subject one or more additional agents. In some embodiments, the additional agent is a corticosteroid (e.g., triamcinolone), and/or a VEGF inhibitor (e.g., ranibizumab, aflibercept intravitreal).

In certain embodiments, the present invention provides a pharmaceutical composition comprising a αA-crystallin protein modulating compound (e.g., a phosphomimetic peptide αA-crystallin protein having a T148D substitution within SEQ ID NO: 1 for human subjects) (e.g., a phosphomimetic peptide αA-crystallin protein having a S148D substitution within SEQ ID NO: 2 for rodent subjects).

In certain embodiments, the present invention provides kits comprising a pharmaceutical composition comprising a αA-crystallin protein modulating compound.

In certain embodiments, the present invention provides methods for determining if a subject is experiencing or is at risk for experiencing diabetic retinopathy through obtaining a biological sample from the subject (e.g., retinal cells) and determining the presence or absence of αA-crystallin protein phosphorylated or not phosphorylated at amino acid 148 (e.g., through post translational modification of protein at amino acid position 148), wherein a determined presence of αA-crystallin protein lacking phosphorylation at amino acid 148 indicates the subject is experiencing or is at risk for experiencing diabetic retinopathy.

BRIEF DESCRIPTION OF DRAWINGS

FIG. 4A-D: αA- and αB-crystallins are primarily expressed by ganglion cells and glial cells under diabetic conditions. Immunohistochemistry for αA- (A-B) and αB-crystallins (C-D) was performed on retinal cross-sections from non-diabetic and diabetic WT mice. Consistent with the protein expression data previously reported, the immunostaining shows increased immunoreactivity of both crystallins in response to diabetes, whereas they are barely detected in non-diabetic controls. Double immunostaining with specific markers of Müller glial cells (gluthamine synthetase) (A, C) and ganglion cells (Neurofilament H) (B, D) reveal colocalization of αA-crystallins with Müller glial cells during diabetes (A) and partial colocalization with ganglion cells (B). Analysis of αB-crystallins shows partial colocalization with Müller glial cells (C) and ganglion cells (D) along with a diffuse signal throughout the retina, suggesting expression of αB-crystallins also in other cell types.

FIG. 5A-D: αA-crystallin is basally induced in the retina of αB-crystallin KO mice. Representative immunoblots for αA- and αB-crystallins on retinal lysates from WT, αA-crystallin KO mice (Ko-CryAA), αB-crystallin KO (Ko-CryAB) and double-KO (Ko-CryAA/AB) (A), and graphic representation of the corresponding quantification (B, C) are shown. Crystallin expression in 12 weeks diabetic (D, n=15) animals is presented normalized to actin levels and relative to the expression of littermate non-diabetic (ND) controls (100%, n=9). αA and αB-crystallin expression is highly unregulated during diabetes in wild-type (WT) diabetic mice. Absence of αA-crystallin (Ko-CryAA) does not affect αB-crystallin expression at baseline, whereas absence of αB-crystallin (Ko-CryAB) lead to an increased upregulation of αA-crystallin already at baseline. As expected neither αA- nor αB-crystallins could be detected in the double knockout (Ko-CryAA/AB) mice. *Significantly different from non-diabetic WT mice (p≤0.01, **p≤0.0001). #Significantly different from WT diabetic mice (#p≤0.05, ###p≤0.01, ####p≤0.001, p≤0.0001).

FIG. 8: Amino acid sequence for wild type human αA-crystallin protein (SEQ ID NO: 1); and amino acid sequence for wild type murine αA-crystallin protein (SEQ ID NO: 2).

DETAILED DESCRIPTION OF THE INVENTION

Figure 1A:
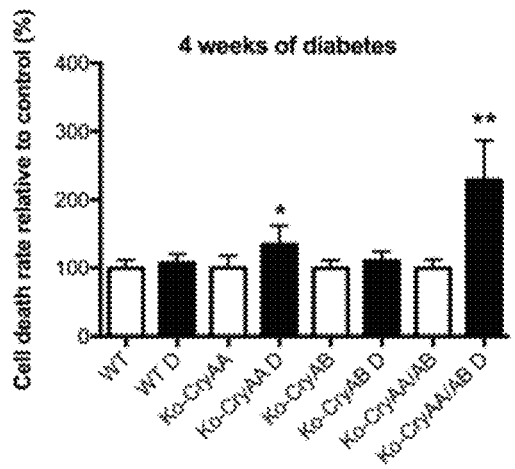
FIG. 1A-C: Loss of αA-crystallin, but not αB-crystallin, leads to increased diabetes-induced retinal cell death. Relative retinal cell death was measured by DNA fragmentation ELISA in whole retinas from WT, αA-crystallin KO mice (Ko-CryAA), αB-crystallin KO (Ko-CryAB) and double-KO (Ko-CryAA/AB) after 4 (A), 8 (B) and 12 (C) weeks of diabetes. αA-crystallin KO mice showed higher levels of retinal cell death at every time point measured, being already significant after 4 weeks of diabetes. αB-crystallin KO mice were associated with lower level of cell death while double-KO also presented with an early and even further significant increase in cell death. *Significantly different from non-diabetic WT mice (*$p \leq 0.05$ or **$p \leq 0.01$). #Significantly different from WT diabetic mice (#$p \leq 0.05$).

Diabetic retinopathy is one of the major complications associated with diabetes and despite significant effort still remains the number one cause of vision loss in the working age population (see, Klein R, Klein B E K. Investigative ophthalmology & visual science. 2013; 54(14)). While recent progress has led to the development of new therapeutic options for a subset of patients with advanced retinopathy, specifically macular edema (see, Amoaku W M, Saker S, et al., Eye (London, England). 2015; 29(9):1115-30), the early stage of the disease remains to be better understood in order to develop more effective treatments. In the past 2 decades, a growing number of studies have demonstrated in animal models and in human patients the neurodegenerative element of diabetic retinopathy especially in the early stages of the disease (see, Barber A J, et al., J Clin Invest. 1998; 102(4):783-91; Martin P M, et al., Invest Ophthalmol Vis Sci. 2004; 45(9):3330-6; Sohn E H, et al., Proceedings of the National Academy of Sciences of the United States of America. 2016; 113(19):64). While perturbations of the neurovascular unit have been clearly shown, the underlying mechanisms of neurodegeneration remain to be clearly established.

It has been demonstrated that neurodegeneration in animal models of diabetes is consistently associated with increased levels of several members of the crystallin protein family (see, Fort P E, et al., Mol Cell Proteomics. 2009; 8(4):767-79; Kumar P A, et al., Arch Biochem Biophys. 2005; 444(2):77-83). Crystallin proteins are grouped in 3 major classes: α-, β-, and γ-crystallins. While the role of γ-crystallins remains poorly understood outside of the ocular lens, α- and β-crystallin proteins have gained increasing interest from the retinal neurodegenerative research community in the past decade as demonstrated by a number of recent publications regarding their potential role in different aspects of retinal diseases including vascular remodeling, neuroinflammation and neurodegeneration (see, Brownell S E, et al., Frontiers in immunology. 2012; 3:74; Sinha D, et al., Mol Cell Neurosci. 2008; 37(1):85-95). While αB- and βA1/A3-crystallins are known to regulate the integrity of the vasculature in the central nervous system, in part through regulation of VEGF function (see, Sinha D, et al., Mol Cell Neurosci. 2008; 37(1):85-95; Kase S, et al., Blood. 2010; 115(16):3398-406), αA- and αB-crystallins have been implicated in regulating neuronal cell survival in multiple neurodegenerative conditions including stroke (see, Arac A, et al., Proc Natl Acad Sci USA. 2011; 108(32):13287-92), endophthalmitis (see, Whiston E A, et al., Infect Immun. 2008; 76(4):1781-90) and uveitis (see, Rao N A, et al., PLoS One. 2012; 7(3); Rao N A, et al., Invest Ophthalmol Vis Sci. 2008; 49(3):1161-71). Both αA- and αB-crystallins are protective in the context of hypoxia (see, Yaung J, et al., Exp Eye Res. 2008; 86(2):355-65), only αA-crystallin demonstrate a protective potential against autoimmune uveitis (see, Rao N A, et al., PLoS One. 2012; 7(3)), suggesting specific and independent mechanisms for different crystallins. This observation is consistent with studies suggesting that in addition to forming heterodimers, αA- and αB-crystallins protect lens epithelial cells via signaling pathways involving activation of Akt and inhibition of RAF/MEK/ERK pathways, respectively (see, Liu J P, et al., Exp Eye Res. 2004; 79(3):393-403).

It was previously demonstrated that numerous crystallin proteins were upregulated in the retina of several animal models of diabetes including the streptozotocin-induced diabetic rats, and mice, as well as the Ins2$^{Akita}$ mouse model (see, Fort P E, et al., Mol Cell Proteomics. 2009; 8(4):767-79; Losiewicz M K, et al., Invest Ophthalmol Vis Sci. 2011; 52(9):5034-42). Recent reports have suggested that α-crystallins also accumulate in ocular tissues of diabetic patients supporting an important role for this stress response in the pathology of diabetic retinopathy (see, Dong Z, Kase S, Ando R, Fukuhara J, Saito W, Kanda A, et al. Alphab-Crystallin Expression in Epiretinal Membrane of Human Proliferative Diabetic Retinopathy. Retina. 2012; Kase S, Ishida S, Rao N A. Increased expression of alphaA-crystallin in human diabetic eye. Int J Mol Med. 2011; 28(4):505-11). It was shown that overexpression of α-crystallins protects retinal neurons in culture, and also that diabetes dramatically reduces their solubility and alters their subcellular localization (see, Losiewicz M K, et al., Invest Ophthalmol Vis Sci. 2011; 52(9):5034-42). Such changes have been highly associated with decreased chaperone activity and protective capacity of αB-crystallin, in part due to post-translational modifications (see, Schmidt T, et al., Cell stress & chaperones. 2016; 21(1):167-78). It was recently reported that αB-crystallin increased levels in diabetes is associated with increased levels of phosphorylation (see, Heise E A, Marozas L M, Grafton S A, Green K M, Kirwin S J, Fort P E. Strain-independent increases of crystallin proteins in the retina of type 1 diabetic rats. PLoS One. 2013; 8(12)), however the nature and impact of αA-crystallin post-translational modification remains less understood.

Experiments conducted during the course of developing embodiments for the present invention demonstrated that αA- and αB-crystallin play very distinct roles in the retina during diabetes despite relatively similar patterns of expression. In particular, such experiments demonstrated the specific role of αA-crystallin in retinal cell survival during diabetes, in part by its role in the regulation of Bax expression and localization. It was also shown how diabetes affects the protective role of αA-crystallin through PTMs and the central role of amino acid 148 phosphorylation.

Accordingly, the invention relates to αA-crystallin protein modulating compounds (e.g., phosphomimetic peptides), compositions comprising such modulating compounds, and their use as therapeutics for the treatment and prevention of conditions involving neurodegeneration and neuroinflammation.

The invention further relates to methods of treating, ameliorating, or preventing disorders in a subject, such as those that are characterized by aberrant αA-crystallin protein activity (e.g., diabetic retinopathy). In some embodiments, the aberrant αA-crystallin protein activity is the result of post translational modification rendering the protein ineffective, such as the loss of phosphorylation at T148 within SEQ ID NO: 1 for human patients and 5148 within SEQ ID NO: 2 for rodents. Such methods comprise, for example, administering to the subject (e.g., a human patient) a composition comprising one or more αA-crystallin protein modulating compounds of the invention and, potentially, additional agent(s).

Such methods are not limited to a particular manner of administration. In some embodiments, the composition is administered through direct injection into the subject's ocular region (e.g., eye).

The present invention is not limited to particular types or kinds of αA-crystallin protein modulating compounds.

In some embodiments, the αA-crystallin protein modulating compound is a compound configured to mimic wild type αA-crystallin protein activity. In some embodiments, the αA-crystallin protein modulating compound is a compound configured to mimic wild type αA-crystallin protein activity phosphorylated at amino acid position 148 within SEQ ID NO: 1 for human subjects and SEQ ID NO: 2 for rodents.

In some embodiments, the αA-crystallin protein modulating compound is a phosphomimetic peptide having an amino acid sequence having a threonine (T) to aspartic acid (D) substitution at amino acid position 148 within SEQ ID NO: 1. In some embodiments, the αA-crystallin protein modulating compound is a phosphomimetic peptide having an amino acid sequence comprising a portion (e.g., 50%, 55%, 60%, 65%, 70%, 75%, 80%, 85%, 90%, 95%, 97%, 98%, 99%, 99.5%, 99.8%, 99.9%, 100%) of SEQ ID NO: 1 having a threonine (T) to aspartic acid (D) substitution at amino acid position 148 and retaining wild type activity. In some embodiments, the αA-crystallin protein modulating compound is a phosphomimetic peptide having an amino acid sequence having a threonine (T) to glutamate (E) substitution at amino acid position 148 within SEQ ID NO: 1. In some embodiments, the αA-crystallin protein modulating compound is a phosphomimetic peptide having an amino acid sequence comprising a portion (e.g., 50%, 55%, 60%, 65%, 70%, 75%, 80%, 85%, 90%, 95%, 97%, 98%, 99%, 99.5%, 99.8%, 99.9%, 100%) of SEQ ID NO: 1 having a threonine (T) to glutamate (E) substitution at amino acid position 148 and retaining wild type activity.

In some embodiments, the αA-crystallin protein modulating compound is a phosphomimetic peptide having an amino acid sequence having a serine (S) to aspartic acid (D) substitution at amino acid position 148 within SEQ ID NO: 2. In some embodiments, the αA-crystallin protein modulating compound is a phosphomimetic peptide having an amino acid sequence comprising a portion (e.g., 50%, 55%, 60%, 65%, 70%, 75%, 80%, 85%, 90%, 95%, 97%, 98%, 99%, 99.5%, 99.8%, 99.9%, 100%) of SEQ ID NO: 2 having a serine (S) to aspartic acid (D) substitution at amino acid position 148 and retaining wild type activity. In some embodiments, the αA-crystallin protein modulating compound is a phosphomimetic peptide having an amino acid sequence having a serine (S) to glutamate (E) substitution at amino acid position 148 within SEQ ID NO: 2. In some embodiments, the αA-crystallin protein modulating compound is a phosphomimetic peptide having an amino acid sequence comprising a portion (e.g., 50%, 55%, 60%, 65%, 70%, 75%, 80%, 85%, 90%, 95%, 97%, 98%, 99%, 99.5%, 99.8%, 99.9%, 100%) of SEQ ID NO: 2 having a serine (S) to glutamate (E) substitution at amino acid position 148 and retaining wild type activity.

In some embodiments, the αA-crystallin protein modulating compound is a small molecule compound structurally configured to mimic wild type αA-crystallin protein activity phosphorylated at amino acid position 148 within SEQ ID NO: 1 or 2.

In some embodiments, the αA-crystallin protein modulating compound is configured to inhibit casepase 3/7 activity.

In some embodiments, the methods further comprise administering to the subject one or more additional agents. In some embodiments, the additional agent is a corticosteroid (e.g., triamcinolone), and/or a VEGF inhibitor (e.g., ranibizumab, aflibercept intravitreal).

In certain embodiments, the present invention provides methods for mimicking the activity of αA-crystallin protein phosphorylated at amino acid 148 in a subject (e.g., human subject, non-human subject), comprising administering to the subject a αA-crystallin protein modulating compound as described herein (e.g., a phosphomimetic peptide αA-crystallin protein having a T148D substitution within SEQ ID NO: 1 for human subjects) (e.g., a phosphomimetic peptide αA-crystallin protein having a S148D substitution within SEQ ID NO: 2 for rodent subjects). In some embodiments, the subject has or is at risk for developing diabetic retinopathy.

An important aspect of the present invention is that the αA-crystallin protein modulating compounds of the invention are capable of inhibiting caspase 3/7 activity within retinal cells. In addition, the αA-crystallin protein modulating compounds of the invention are capable of mimicking wild type αA-crystallin protein activity phosphorylated at amino acid position 148. Moreover, the αA-crystallin protein modulating compounds of the invention are capable of treating and/or preventing diabetic retinopathy related to aberrant αA-crystallin protein activity (e.g., aberrant αA-crystallin protein activity resulting from post translational modification rendering the protein incapable of phosphorylation at amino acid position 148).

Some embodiments of the present invention provide methods for administering an effective amount of a αA-crystallin protein modulating compound of the invention of the invention and at least one additional therapeutic agent (e.g., a therapeutic agent for treating and/or preventing diabetic retinopathy (e.g., a corticosteroid (e.g., triamcinolone), and/or a VEGF inhibitor (e.g., ranibizumab, aflibercept intravitreal)).

In some embodiments of the present invention, a αA-crystallin protein modulating compound of the invention and one or more therapeutic agents (e.g., a therapeutic agent for treating and/or preventing diabetic retinopathy) are administered to an animal under one or more of the following conditions: at different periodicities, at different durations, at different concentrations, by different administration routes, etc. In some embodiments, the αA-crystallin protein modulating compound is administered prior to the therapeutic agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic agent. In some embodiments, the αA-crystallin protein modulating compound is administered after the therapeutic agent, e.g., 0.5, 1, 2, 3, 4, 5, 10, 12, or 18 hours, 1, 2, 3, 4, 5, or 6 days, or 1, 2, 3, or 4 weeks after the administration of the therapeutic agent. In some embodiments, the αA-crystallin protein modulating compound and the therapeutic agent are administered concurrently but on different schedules, e.g., the αA-crystallin protein modulating compound is administered daily while the therapeutic agent is administered once a week, once every two weeks, once every three weeks, or once every four weeks. In other embodiments, the αA-crystallin protein modulating compound is administered once a week while the therapeutic agent is administered daily, once a week, once every two weeks, once every three weeks, or once every four weeks.

Compositions within the scope of this invention include all compositions wherein the αA-crystallin protein modulating compounds of the present invention are contained in an amount which is effective to achieve its intended purpose. While individual needs vary, determination of optimal ranges of effective amounts of each component is within the skill of the art. Typically, the αA-crystallin protein modulating compounds may be administered to mammals, e.g. humans, orally at a dose of 0.0025 to 50 mg/kg, or an equivalent amount of the pharmaceutically acceptable salt thereof, per day of the body weight of the mammal being treated. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the αA-crystallin protein modulating compound. The unit dose may be administered one or more times daily as one or more tablets or capsules each containing from about 0.1 to about 10 mg, conveniently about 0.25 to 50 mg of the αA-crystallin protein modulating compound or its solvates.

In a topical formulation, the αA-crystallin protein modulating compound may be present at a concentration of about 0.01 to 100 mg per gram of carrier. In a one embodiment, the αA-crystallin protein modulating compound is present at a concentration of about 0.07-1.0 mg/ml, for example, about 0.1-0.5 mg/ml, and in one embodiment, about 0.4 mg/ml.

In addition to administering the αA-crystallin protein modulating compound as a raw chemical, such may be administered as part of a pharmaceutical preparation containing suitable pharmaceutically acceptable carriers comprising excipients and auxiliaries which facilitate processing of the αA-crystallin protein modulating compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active αA-crystallin protein modulating compound(s), together with the excipient.

The pharmaceutical compositions of the invention may be administered to any patient which may experience the beneficial effects of the αA-crystallin protein modulating compounds of the invention. Foremost among such patients are mammals, e.g., humans, although the invention is not intended to be so limited. Other patients include veterinary animals (cows, sheep, pigs, horses, dogs, cats and the like).

The αA-crystallin protein modulating compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active αA-crystallin protein modulating compounds in water-soluble form, for example, water-soluble salts and alkaline solutions. In addition, suspensions of the active αA-crystallin protein modulating compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

It was previously demonstrated that diabetes was associated with increased crystallin protein levels in both stz-induced diabetic rats and mice (see, Fort P E, et al., Mol Cell Proteomics. 2009; 8(4):767-79; Losiewicz M K, Fort P E. Invest Ophthalmol Vis Sci. 2011; 52(9):5034-42). It was specifically showed that both αA- and αB-crystallins accumulated in the retina of both of those models of diabetes.

In order to gain a better understanding about the role of each α-crystallin protein, experiments were conducted that induced diabetes by stz injection in mice lacking expression of αA-crystallin (Ko-CryAA), αB-crystallin (Ko-CryAB) or both (Ko-CryAA/AB). The animals were followed over time to control for similar disease conditions throughout the study (Table 1). As expected, no significant differences were noted regarding body weight or blood glucose levels suggesting that the absence of crystallin had no impact on the animals' sensitivity to diabetes induction or level of sickness. This point was confirmed by post-mortem analysis of the pancreas, which demonstrated no difference in weight and islet content irrespective of the genotype.

Type 1 diabetes reduces retinal thickness in patients with minimal to no vascular lesions (see, Sohn E H, et al., Proc Natl Acad Sci USA. 2016; 113(19)) so experiments were conducted to further analyze the impact of diabetes on the neuroretina by performing a longitudinal analysis of the retinal thickness by optical coherence tomography (OCT). Consistent with the DNA fragmentation data, thinning of the retina was observed very early in the αA-crystallin-knockout mice but not in the αB-crystallin knockout mice (FIG. 2). This analysis demonstrated thinning of the retina of αA-crystallin-knockout mice as early as 2 weeks post-diabetes induction, and enhanced after 4 weeks of diabetes. Unfortunately, lack of αA-crystallin or both αA- and

TABLE 1

Metabolic information and number of animals for each experimental group used.

| | Blood glucose (mg/dl) | | | | | | | | | | | | | | | |
|---|---|---|---|---|---|---|---|---|---|---|---|---|---|---|---|---|
| | WT | | | | Ko-CryAA | | | | Ko-CryAB | | | | Ko-CryAA/AB | | | |
| | Non Diabetic Avg. | Non Diabetic STD. | Diabetic Avg. | Diabetic STD. | Non Diabetic Avg. | Non Diabetic STD. | Diabetic Avg. | Diabetic STD. | Non Diabetic Avg. | Non Diabetic STD. | Diabetic Avg. | Diabetic STD. | Non Diabetic Avg. | Non Diabetic STD. | Diabetic Avg. | Diabetic STD. |
| 4 wks | 108.1 | 14.6 | 565.2 | 51.1 | 115.0 | 13.2 | 562.3 | 47.0 | 113.4 | 14.4 | 516.2 | 73.5 | 120.3 | 15.8 | 524.8 | 77.1 |
| 8 wks | 123.8 | 19.7 | 441.9 | 73.4 | 118.6 | 30.9 | 452.2 | 84.8 | 120.8 | 21.8 | 488.9 | 82.2 | 133.6 | 16.1 | 509.1 | 59.8 |
| 12 wks | 129.1 | 19.3 | 449.4 | 92.4 | 131.9 | 27.2 | 474.5 | 88.2 | 129.6 | 21.4 | 468.5 | 87.1 | 129.5 | 18.7 | 501.9 | 90.5 |
| 20 wks | 105.5 | 6.8 | 393.2 | 103.7 | 94.8 | 5.6 | 406.5 | 126.2 | 108.8 | 7.8 | 387.6 | 96.5 | 106.6 | 2.9 | 345.5 | 90.3 |

| | body weight (g) | | | | | | | | | | | | | | | |
|---|---|---|---|---|---|---|---|---|---|---|---|---|---|---|---|---|
| | WT | | | | Ko-CryAA | | | | Ko-CryAB | | | | Ko-CryAA/AB | | | |
| | Non Diabetic Avg. | Non Diabetic STD. | Diabetic Avg. | Diabetic STD. | Non Diabetic Avg. | Non Diabetic STD. | Diabetic Avg. | Diabetic STD. | Non Diabetic Avg. | Non Diabetic STD. | Diabetic Avg. | Diabetic STD. | Non Diabetic Avg. | Non Diabetic STD. | Diabetic Avg. | Diabetic STD. |
| 4 wks | 19.7 | 1.7 | 21.3 | 2.3 | 22.4 | 2.0 | 19.0 | 1.9 | 23.9 | 2.0 | 21.4 | 1.6 | 22.8 | 1.9 | 22.0 | 3.1 |
| 8 wks | 26.1 | 3.6 | 20.8 | 3.0 | 24.0 | 3.0 | 21.9 | 2.4 | 23.6 | 2.8 | 20.4 | 1.9 | 28.1 | 3.2 | 20.9 | 1.6 |
| 12 wks | 28.4 | 3.8 | 22.3 | 2.3 | 25.2 | 3.1 | 21.2 | 3.3 | 25.9 | 2.6 | 20.1 | 3.2 | 27.4 | 3.9 | 22.2 | 3.3 |
| 20 wks | 27.3 | 4.1 | 26.8 | 3.1 | 26.0 | 4.5 | 24.1 | 3.5 | 27.3 | 1.6 | 22.8 | 3.7 | 29.2 | 3.1 | 25.3 | 3.4 |

Figure 1B:
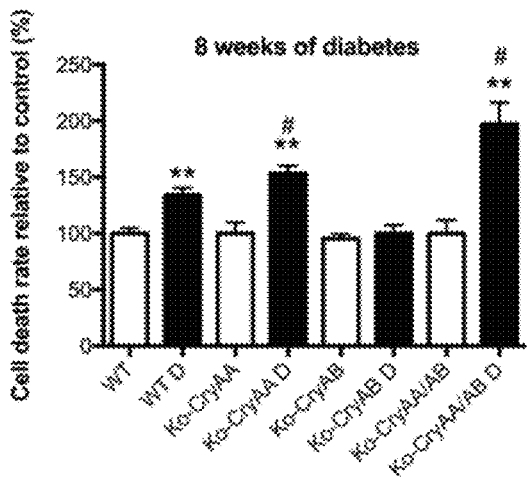
Figure 1C:
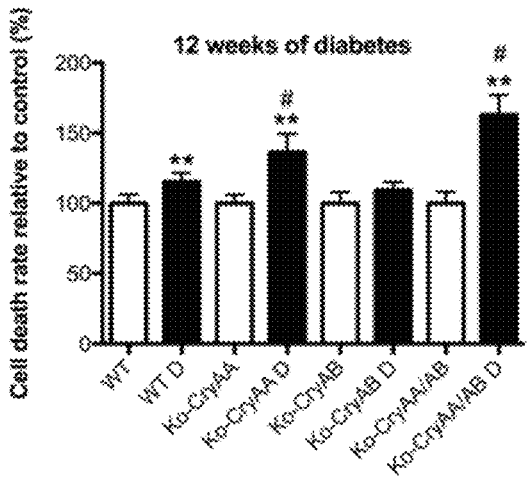
Figure 2A:
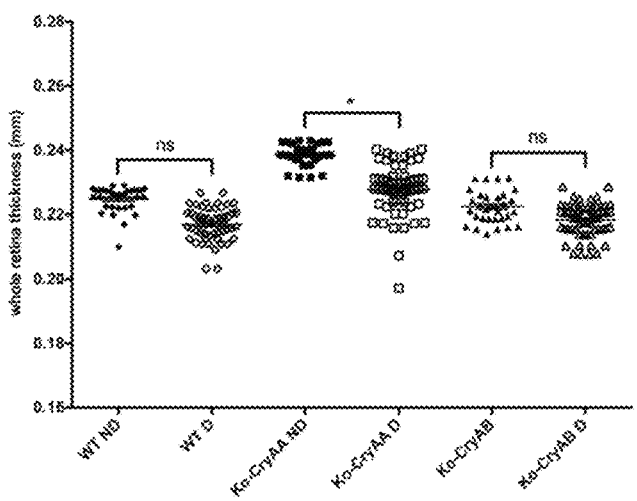
FIG. 2A-D: Loss of αA-crystallin, but not αB-crystallin, leads to enhanced diabetes-induced retinal thinning. Retinal thickness was measured by optical coherence tomography (OCT) in WT, αA-crystallin KO mice (Ko-CryAA), αB-crystallin KO (Ko-CryAB) after 2 (A), 4 (B) 12 (C) and 20 (D) weeks of diabetes. Retinal thickness was reduced in αA-crystallin KO mice as early as 2 weeks after diabetes onset. A similar thinning was detectable in WT mice after 4 weeks of diabetes, at which point the thinning was further enhanced in the αA-crystallin KO. Because of cataract formation OCT could only be done in WT and αB-crystallin Ko mice at later time points and revealed a stabilized effect in WT mice. Only a transient thinning after 4 weeks of diabetes was detected in αB-crystallin KO mice. Early cataract formation makes it impossible to utilize this technique in double-KO mice. *Significantly different from non-diabetic WT mice (*$p \leq 0.05$ or **$p \leq 0.01$).
Figure 2B:
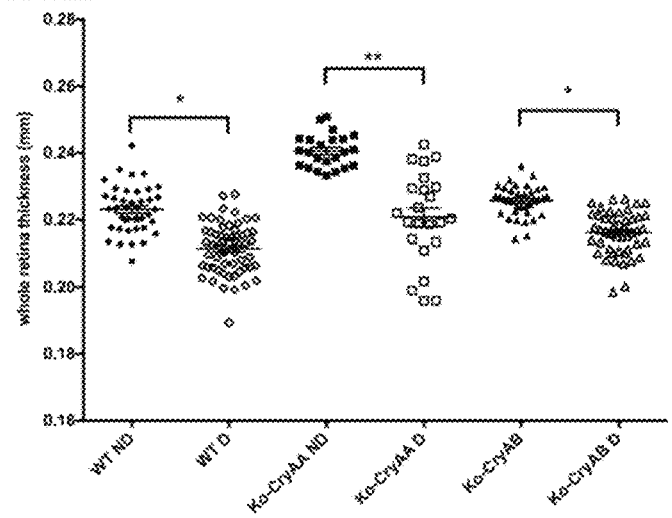
Figure 2C:
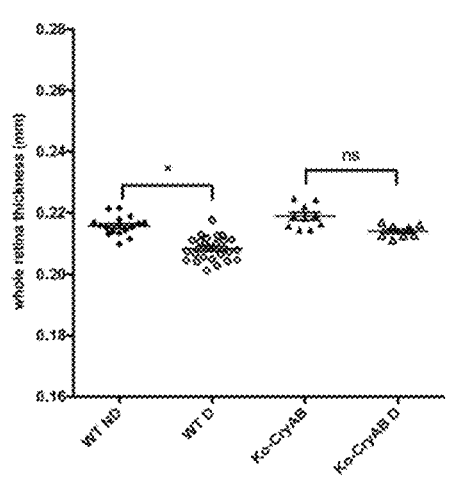
Figure 2D:
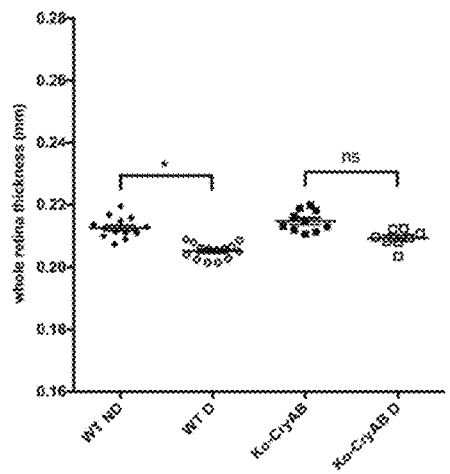

| | number of animals | | | | | | | |
|---|---|---|---|---|---|---|---|---|
| | WT | | Ko-CryAA | | Ko-CryAB | | Ko-CryAA/AB | |
| | Non Diabetic | Diabetic | Non Diabetic | Diabetic | Non Diabetic | Diabetic | Non Diabetic | Diabetic |
| 4 wks | 18 | 22 | 18 | 22 | 17 | 20 | 20 | 23 |
| 8 wks | 18 | 19 | 16 | 18 | 19 | 22 | 9 | 13 |
| 12 wks | 34 | 41 | 16 | 19 | 24 | 17 | 16 | 16 |
| 20 wks | 9 | 22 | 13 | 32 | 9 | 22 | 13 | 24 |

α-Crystallins are protective in several animal models of retinal neurodegenerative diseases, so experiments were conducted to assess the impact of the lack of αA and/or αB-crystallin on retinal cell survival. Using DNA fragmentation as a read-out, experiments performed a time-course analysis of retinal cell death. As previously reported, increased cell death was continuously observed in wild-type animals starting 8 weeks post diabetes induction. As predicted, it was found that αA-crystallin knockout mice consistently had a higher level of retinal cell death, already different after 4 weeks of diabetes (FIG. 1), supporting a neuroprotective role of αA-crystallins. However, such experiments unexpectedly discovered that lack of αB-crystallin was consistently associated with a reduced level of cell death compared to wild-type diabetic mice. Despite this seemingly protective effect of lack of αB-crystallin, concomitant loss of both α-crystallin proteins enhanced diabetes-induced retinal cell death as shown by the significant increase in double-knockout mice (FIG. 1).

αB-crystallin proteins is associated with progressive cataract formation prohibiting the OCT analysis to be performed past 14 and 7 weeks of age, respectively. This limitation prevented the use of this method in the double-knockout mice and past 4 weeks of diabetes in the αA-crystallin knockout. Significant thinning of the retina was observed in wild-type however only starting 4 weeks after diabetes induction and detectable up to 20 weeks post-diabetes induction (FIG. 2D) consistent with the progressive neurodegenerative impact of diabetes on the neuroretina seen in patients. αB-crystallin-knockout mice exhibited retinal thinning after 4 weeks of diabetes although this effect was smaller, consistent with the cell death results and a lower sensitivity to diabetes.

Figure 3A:
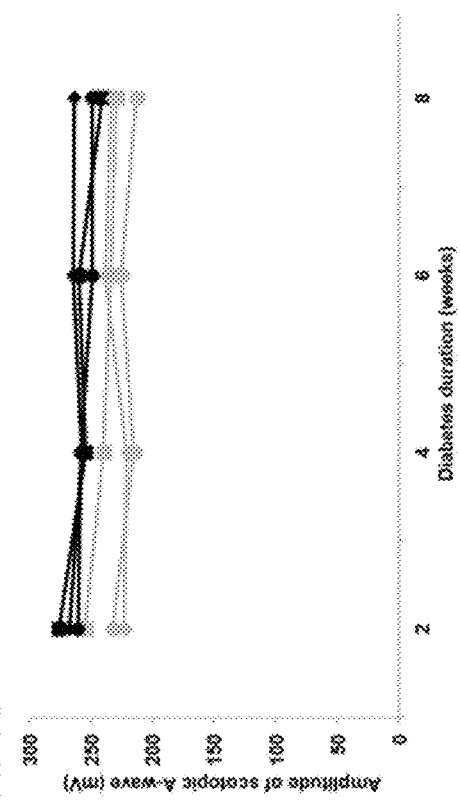
FIG. 3A-D: Loss of either αA-crystallin or αB-crystallin, leads to enhanced diabetes-induced decreased scotopic retinal activity. Retinal activity was evaluated by measuring the electrical response of the retina to light stimuli of various intensities (electroretinogram: ERG) in WT, αA-crystallin KO mice (Ko-CryAA), αB-crystallin KO (Ko-CryAB). We observed a significant decrease of the amplitude of the b-wave (A) and the b to a wave ratio (C) but not the amplitude of the a-wave (B) in diabetic WT animals (grey squares) under scotopic conditions. Consistent with the cell death data, αA-crystallin KO (grey diamonds) mice demonstrated reduced retinal function earlier than WT mice, supporting an hypersensitivity to diabetes. While not affecting cell survival, absence of αB-crystallin (grey circles) was associated with decreased retinal function. Consistent with previous reports, diabetes does not affect the amplitude of the a-wave (B) or photophic response (D), whether α-crystallins are present or not. *Significantly different from non-diabetic WT mice (*p≤0.05 or **p≤0.01). #Significantly different from WT diabetic mice (#p≤0.05).
Figure 3B:
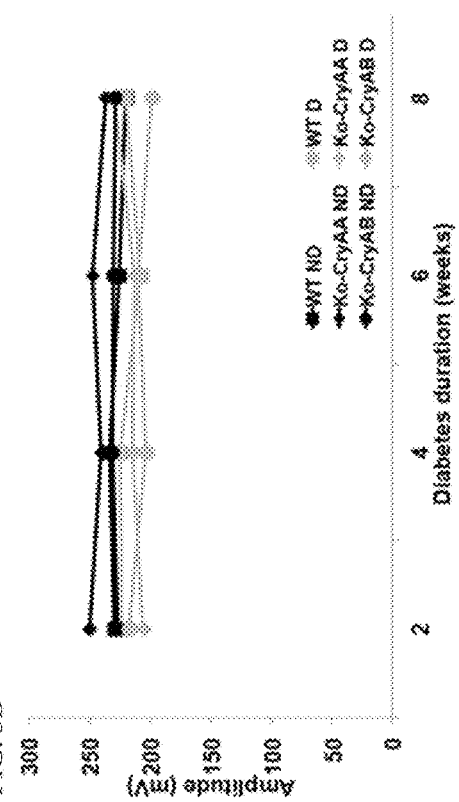
Figure 3C:
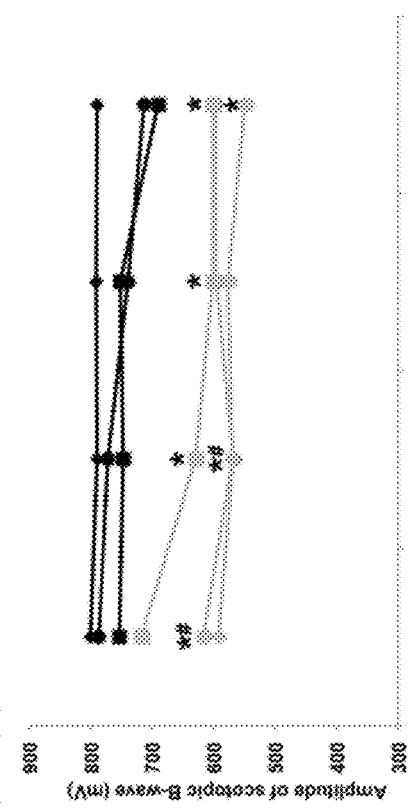
Figure 3D:
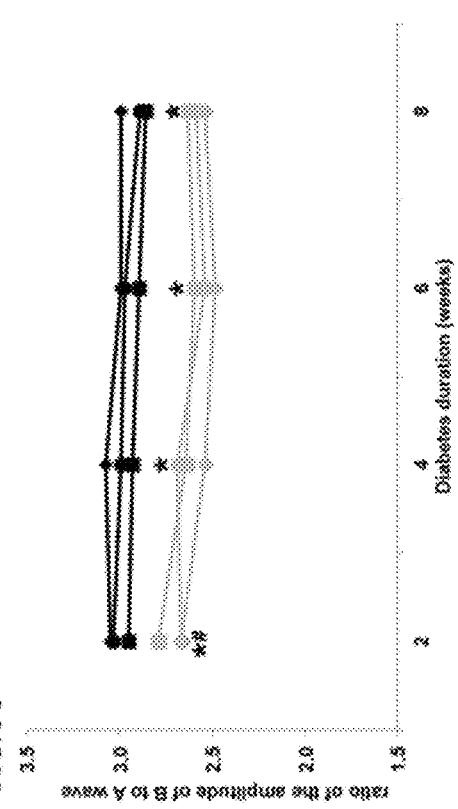

These data suggested acceleration of the progressive neurodegeneration of the retina specifically in the absence of αA-, but not αB-crystallin, and prompted assessment of how retinal function is affected. Retinal function can be evaluated by measuring the electrical response of the retina to light stimuli of various intensities, the recording of which is called electroretinogram (ERG). Consistent with previous reports, it was observed that wild-type animals have a significant and progressive impact of diabetes on the amplitude of the b-wave in dark-adapted (scotopic) conditions (FIG. 3). Lack of αA-crystallin led to an early decrease in retinal function in parallel with the early cell death, αA-crystallin knockout mice demonstrated a reduction in the amplitude of the b-wave in scotopic conditions as early as 2 weeks after diabetes induction (FIG. 3B). As for αB-crystallin, its loss did not affect cell survival and retinal thickness, however it is associated with early decreased retinal function (FIG. 3B), suggesting that αB-crystallin while not critical for retinal cell survival is important for retinal function. The lack of impact of diabetes, whether or not alpha-crystallins are expressed, on the amplitude of the A-wave (FIG. 3B) as well as on the light-adapted (photopic) responses (FIG. 3D) is consistent with previous reports and supports a primary impact on the inner retina. Next, retinal cross-sections were used to analyze the cellular localization of αA- and αB-crystallins in response to diabetes. Previous findings in diabetic rats with a pan-specific antibody recognizing both alpha-crystallins revealed primary expression in the inner retina; hence, experiments co-labeled with specific markers of Müller glial cells (glutamine synthetase) and ganglion cells (Neurofilament-H). Immunostaining on retinal tissue from wild-type animals confirmed that αA- and αB-crystallin were barely detectable in non-diabetic animals (FIG. 4). Similar analysis performed on diabetic tissues revealed increased αA-crystallin immunoreactivity. The signal co-localized with glutamine synthetase, indicating that αA-crystallin is highly expressed by Müller glial cells during diabetes (FIG. 4A), and partially with neurofilament-H (FIG. 4B), suggesting that αA-crystallin is also expressed in ganglion cells. The cellular localization of αB-crystallin showed a similar pattern with a partial co-localization with glutamine synthetase (FIG. 4C) and NF-H (FIG. 4D), along with a diffuse signal throughout the retina suggesting a slight differential expression in other retinal cells. The specificity of the signal was demonstrated by an absence of immuno-reactivity when using retina and lenticular tissue from knockout animals.

To further understand why the absence of αA- but not αB-crystallin leads to increased retinal cell death in response to diabetes, experiments analyzed the expression of αA-crystallin in αB-crystallin knockout and vice-versa. In doing so, it was observed that αB-crystallin knockout mice, which showed no cell death early but functional perturbation, demonstrated a basal induction of αA-crystallin, even in absence of diabetes (FIG. 5). This result suggests that αB-crystallin knockout mice might be protected not due to the absence of αB-crystallin but rather because of the protective function of basally induced αA-crystallin. Conversely, αA-crystallin knockout mice, which showed enhanced cell death under diabetes conditions showed no induction of αB-crystallin at baseline (FIG. 5). Together, these data further support the protective role of αA-crystallin induction during the early stages of diabetes.

Figure 6:
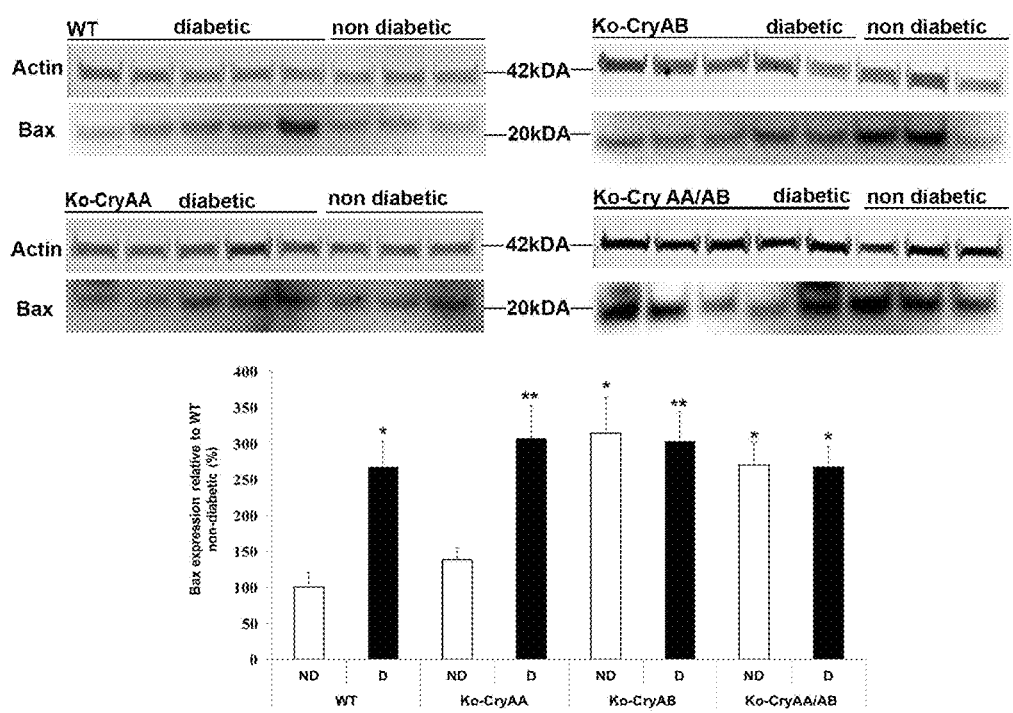
FIG. 6: αA-crystallin does not protect retinal cells from diabetes-induced upregulation of Bax but from its activation. Representative images of immunoblots for Bax on retinal lysates from WT, αA-crystallin KO mice (Ko-CryAA), αB-crystallin KO (Ko-CryAB) and double-KO (Ko-CryAA/AB) (A), and graphic representation of the corresponding quantification (B) are shown. Bax expression in 12 weeks diabetic (D, n=10) animals is presented normalized to actin levels and relative to the expression of littermate non-diabetic (ND) controls (100%, n=6). This analysis shows that while wild-type (WT) and αA-crystallin knockout (Ko-CryAA) animals show significantly higher Bax content under diabetic conditions and that Bax content is not increased by diabetes, but rather high in basal condition, in αB-crystallin KO (Ko-CryAB) or double KO (Ko-CryAA/AB) mice. *Significantly different from non-diabetic WT mice (*p≤0.05, **p≤0.01).

Experiments previously showed that alpha-crystallins interact with the pro-apoptotic protein Bax (see, Losiewicz M K, et al., Invest Ophthalmol Vis Sci. 2011; 52(9):5034-42), so experiments were conducted to determine if αA-crystallin induction would change Bax expression. Wild-type and αA-crystallin knockout mice showed significantly higher retinal Bax under diabetic conditions compared to age-matched non-diabetic mice (FIG. 6), while αB-crystallin knockout mice did not, consistent with the neurodegeneration data.

If increased expression of αA-crystallin in the αB-crystallin knockout mice is protective, it was questioned why are wild-type animals, with progressively increased levels of αA-crystallins during diabetes still exhibiting abnormal cell death. αB-crystallin chaperone function is highly regulated by post-translational modification, and data showed that both αA- and αB-crystallins are targeted by PTMs in the context of diabetes with multiple spots of varying mass and charges in 2D-GEL analysis (see, Fort P E, et al., Mol Cell Proteomics. 2009; 8(4):767-79).

Therefore, experiments were conducted wherein αA-crystallin was immunoprecipitated from retinal tissues of WT diabetic and non-diabetic animals and PTMs were analyzed by tandem mass spectrometry (MS). This analysis revealed the potential phosphorylation of serine residues 122, 148, 155 and 173 of αA-crystallin in normal rodent retina. To further quantify the impact of diabetes on the phosphorylation of these amino acids, and since no antibodies were available, multiple reaction monitoring (MRM) was performed. The three αA-crystallin products detected by immunoblot analysis (see FIG. 5) were isolated by gel separation after immunoprecipitation and revealed a specific effect of diabetes on the level of phosphorylation of the 146-157 peptide. FIG. 7 shows the ratio of phosphorylated to non-phosphorylated 146-157 peptides in diabetic samples relative to the non-diabetic for the three αA-crystallin products in three independent MRM experiments. This clearly shows that the relative amount of phosphorylation on Ser148 was reduced on average by 40-50% after 3 months of diabetes (FIG. 7), suggesting that this specific phosphosite could play a significant role in the dysregulation of αA-crystallin function by diabetes.

Figure 7A:
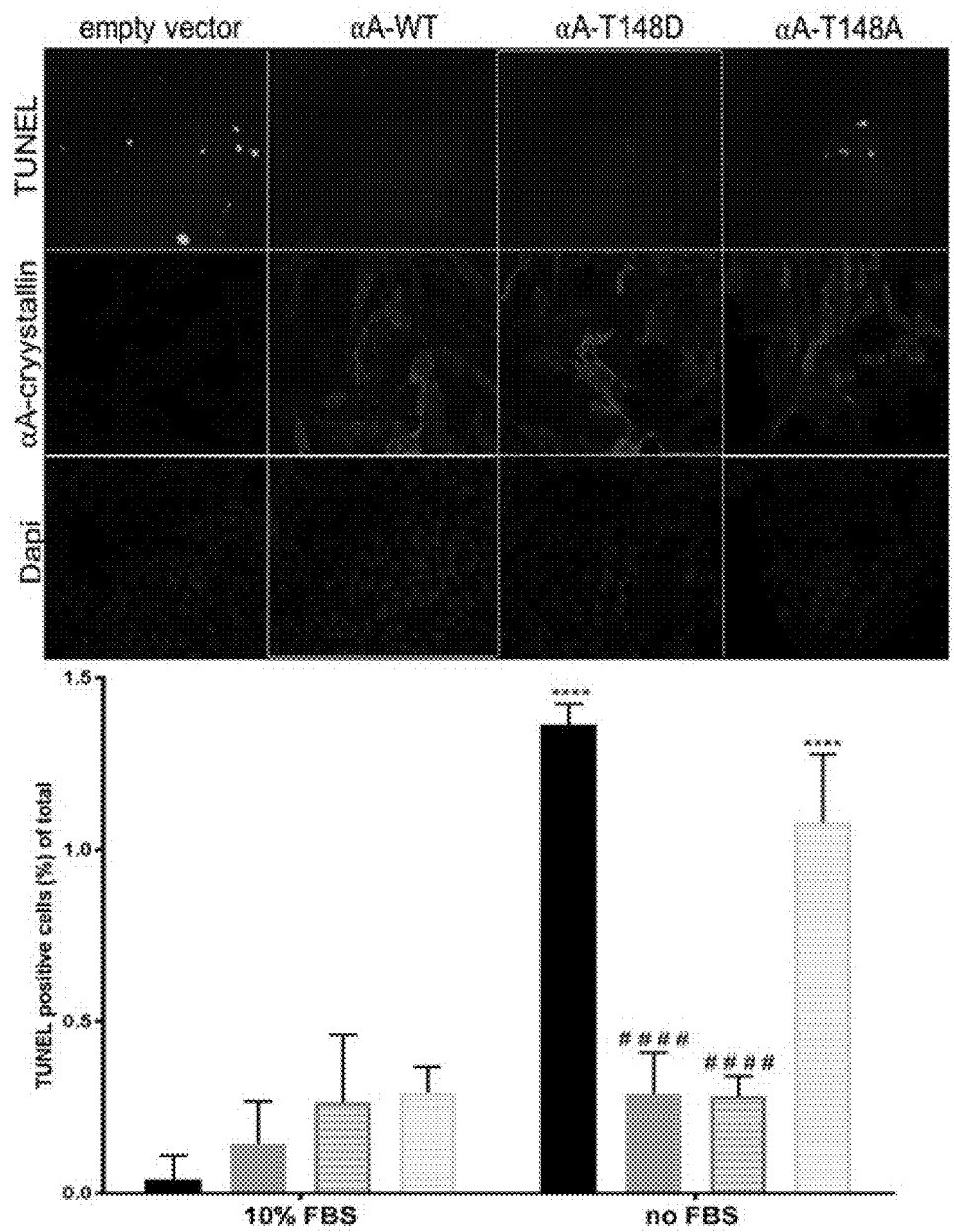
FIG. 7A-F: Impact of α-crystallin phosphorylation on retinal neuronal and glial cell survival. Overexpression of mutants mimicking specific phosphorylation of αA-crystallin (αA T148D) or αB-crystallin (αB STD, αB STA) inversely affect the protection of neuronal and glial cells against serum deprivation-induced cell death, assessed by TUNEL staining (A), DNA fragmentation (B, D) and Caspase 3/7 activity assay (C, E). The expression of mutants mimicking unphosphorylation of αA-crystallin (αA T148A) results in loss of protection, while similar manipulation of αB-crystallin increases protection. Immunoblot analysis of the expression of αA- and αB-crystallin wild type (WT) proteins and their distinct mutants in transfected R28 and rMC1 cells (F), compared to lens sample. Beta-actin served as loading control. *Significantly different from cells in 10% FBS transfected with empty vector (=control) with p≤0.05 or p≤0.01 or *p≤0.001 or ****p≤0.0001. #Non significantly different from control with p>0.05.
Figure 7A:
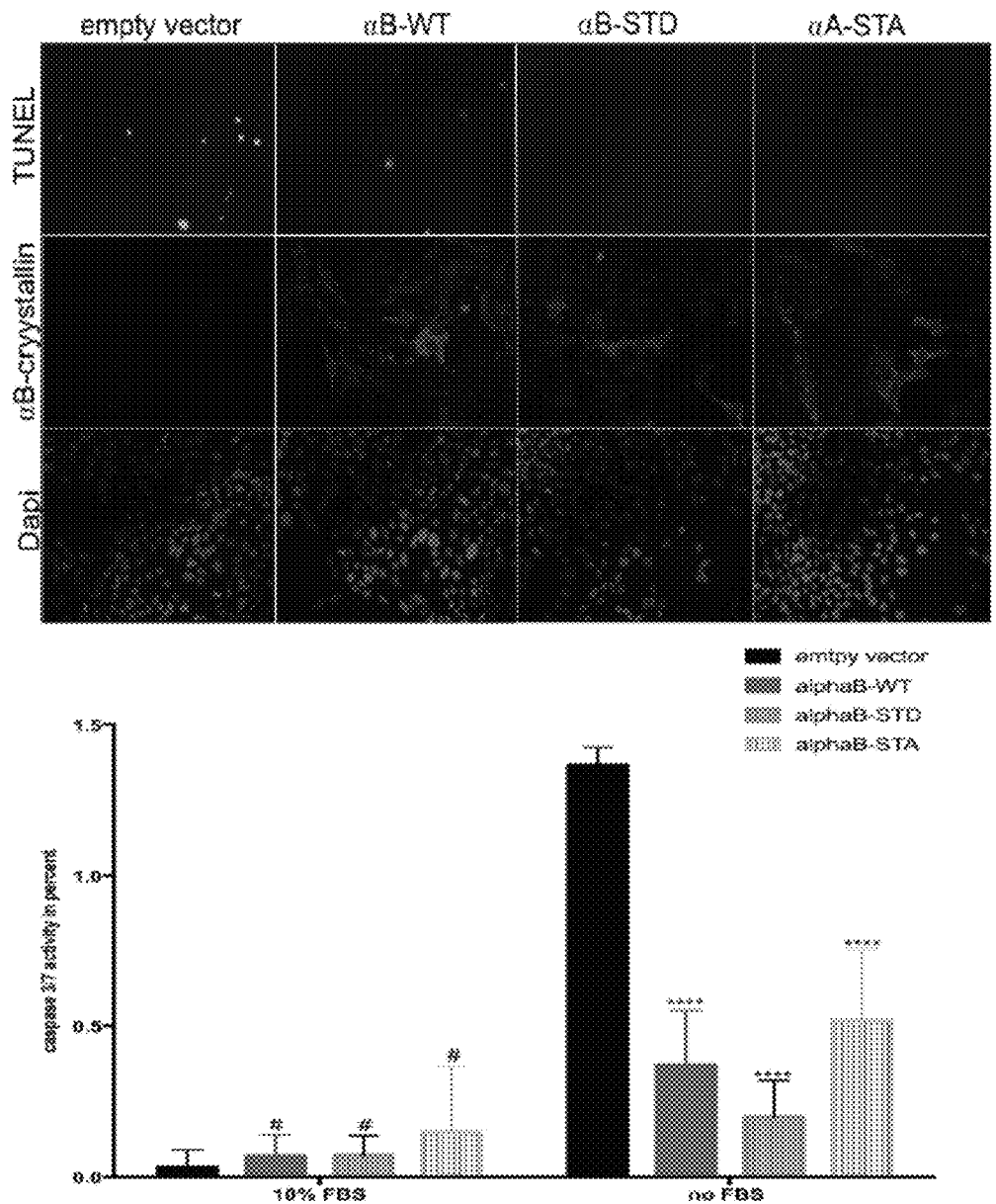
Figure 7B:
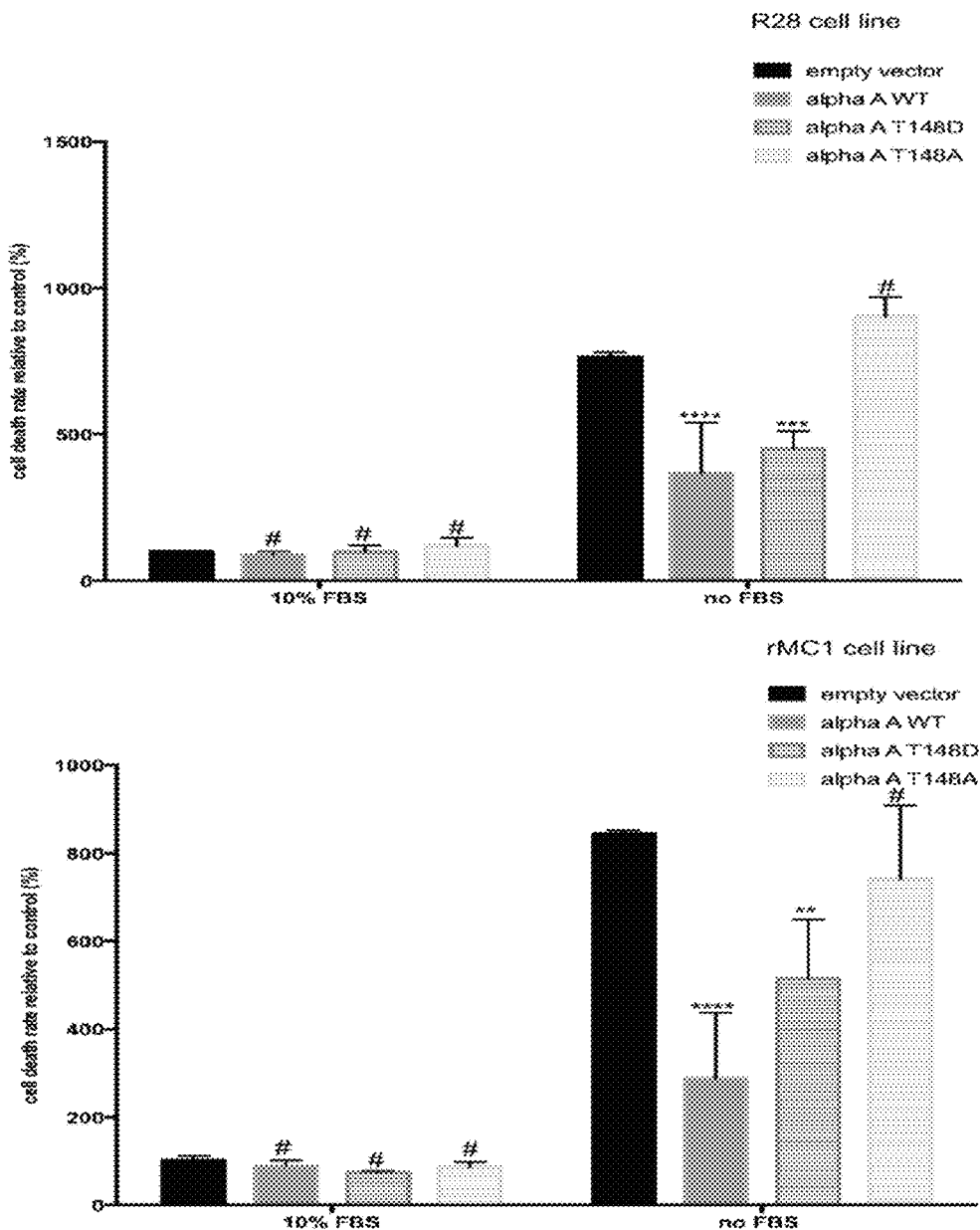
Figure 7C:
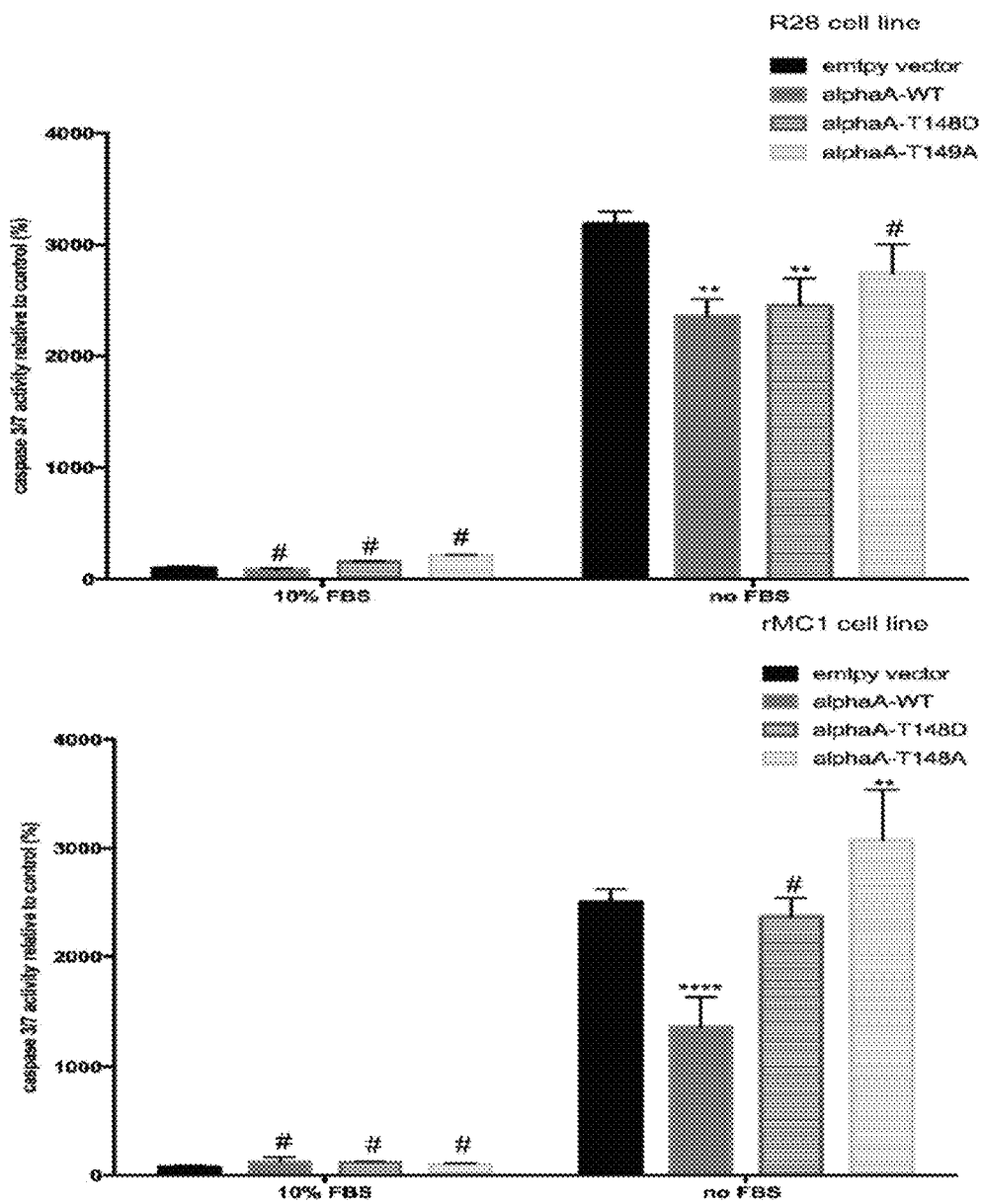
Figure 7D:
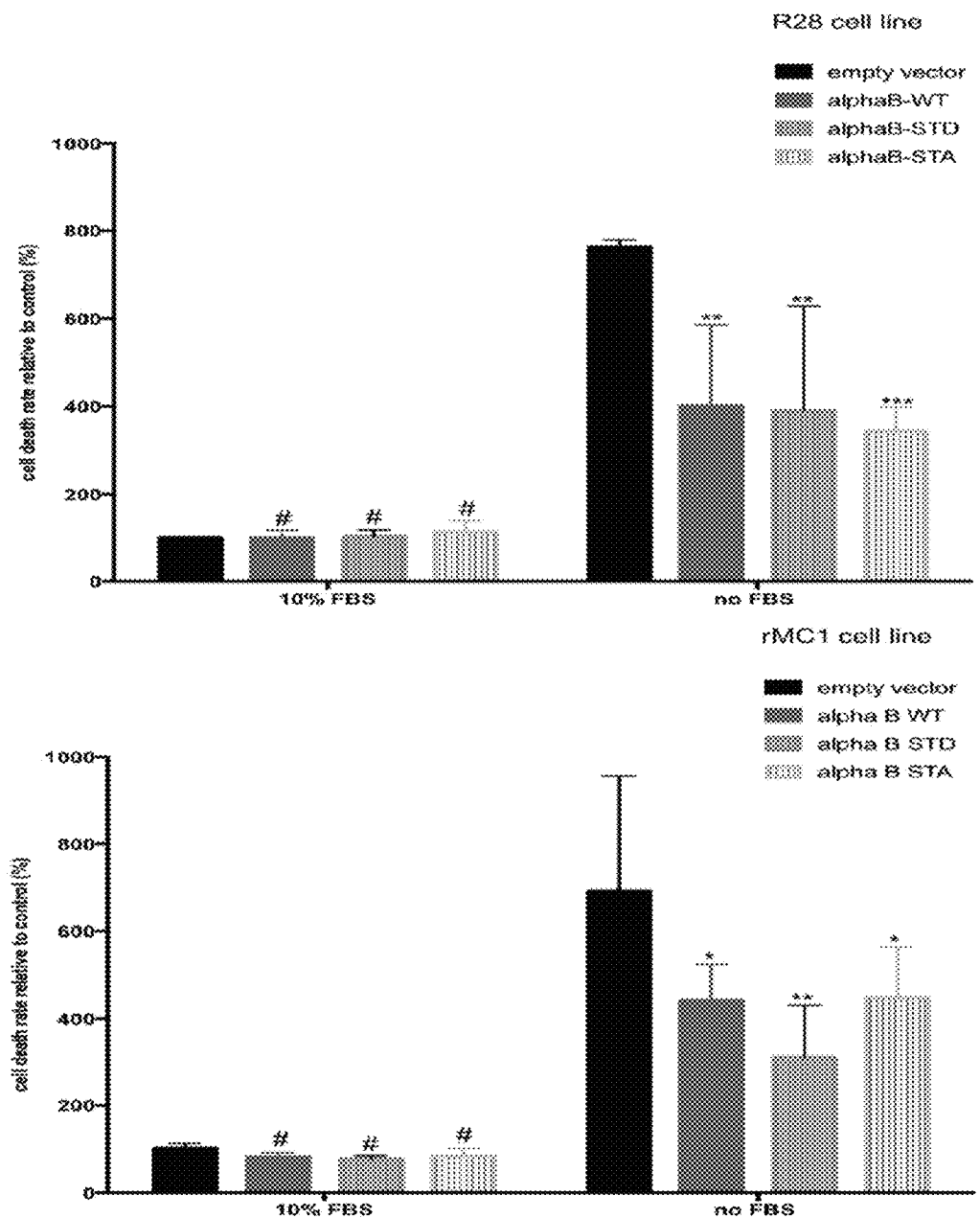
Figure 7E:
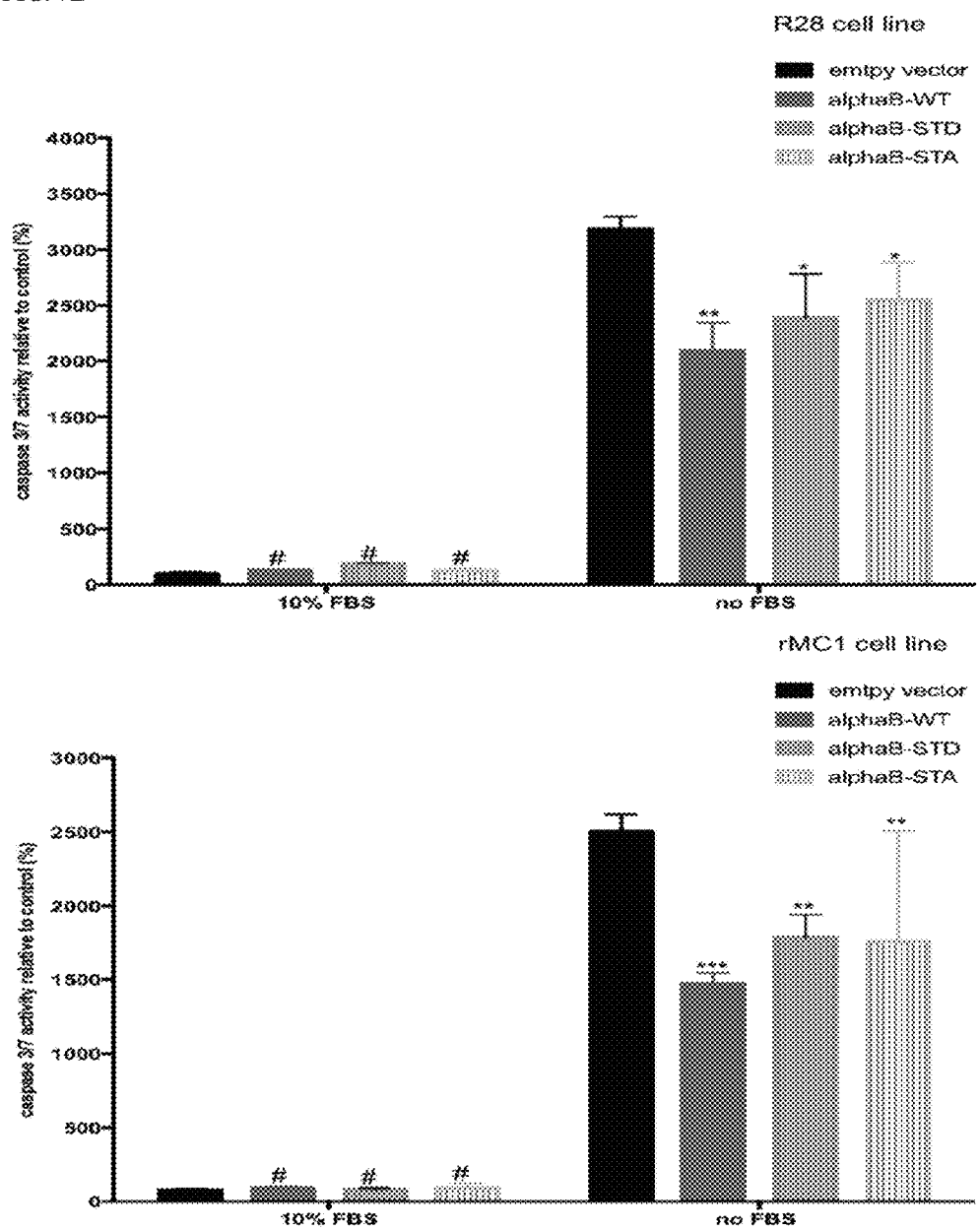
Figure 7F:
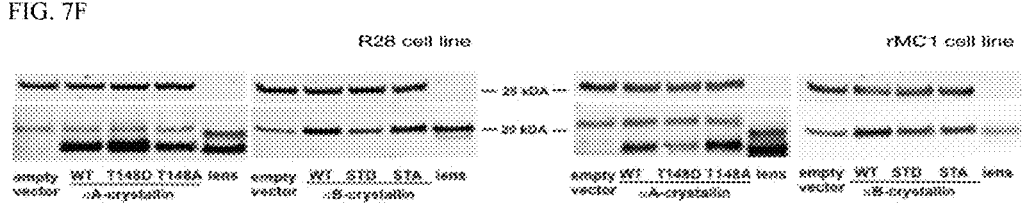

In order to test the impact of this phosphosite on the neuroprotective function of αA-crystallin in retinal neurons, experiments were conducted with a cell culture model. Differentiated R28 rat retinal neuron cells were transfected with constructs expressing either wt, the phosphomimetic (148D) or non-phosphorylatable (148A) mutant of human αA-crystallin. Western-blot and immunofluorescence analysis of the transfected cells showed that all 3 constructs lead to similar transfection efficiency and level of expression of αA-crystallin (FIG. 7B—red channel). As previously reported, transfection with the wt αA-crystallin is protective against metabolic stress-induced cell death measured by TUNEL staining or DNA fragmentation assay (FIG. 7B-C). While the phosphomimetic 148D mutant was just as protective as the wt protein, the non-phosphorylatable 148A mutant showed an almost complete lack of protection consistent with a key regulatory function of this phosphorylation. Further analysis demonstrated that this regulation of apoptosis was at least partially through prevention of caspases-3/7 activation. Overexpression of wt αA-crystallin or its phosphomimetic mutant significantly reduced caspase activation, an effect not seen when overexpressing the non-phosphorylatable mutant of αA-crystallin (FIG. 7D).

Example II

This example provides the materials and methods for Example I.

Induction of Diabetes

Mice were housed under a 12 h light/dark cycle with free access to standard mouse chow and water. All experiments were conducted in accordance with the Association for Research in Vision and Ophthalmology Resolution on the Care and Use of Laboratory Animals. αA- and αB-crystallin knockout mice are a generous gift from Dr. Eric Wawrousek (NIH) and have been previously characterized and described (see, Brady J P, et al., Proc Natl Acad Sci USA. 1997; 94(3):884-9; Brady J P, et al., Invest Ophthalmol Vis Sci. 2001; 42(12):2924-34). Double-knockouts and WT were obtained by breeding the single knockouts together. Diabetes was induced by a total of three intra-peritoneal injections of streptozotocin (STZ) (50 mg/kg; Sigma) dissolved in 10 mM sodium citrate buffer, pH 4.5 while age-matched non-diabetic controls were generated by injection of equivalent volumes of buffer alone. Mice were considered diabetic when exhibiting blood glucose levels >13.9 mmol/1(250 mg/dl; One-Touch meter; Lifescan). The various durations of diabetes were chosen because of the previously reported increased neuronal cell death, microvascular leakage, astrocyte defects, microglial cell activation, and impaired insulin receptor signaling in rat models of insulin deficient diabetes (see, Barber A J, et al., J Clin Invest. 1998; 102(4):783-91; Antonetti D A, et al., Diabetes. 1998; 47(12):1953-9; Barber A J, et al., Invest Ophthalmol Vis Sci. 2000; 41(11):3561-8; Reiter C E, et al., Am J Physiol Endocrinol Metab. 2003; 285(4):E763-74; Zeng X X, et al., Vis Neurosci. 2000; 17(3):463-71) and Ins2$^{Akita}$ mice (see, Barber A J, et al., Invest Ophthalmol Vis Sci. 2005; 46(6):2210-8).

Retinal Anatomy and Visual Function Analysis

Mice were anesthetized with an intra-peritoneal injection of Ketamine (93 mg/kg) and Xylazine (8 mg/kg). Pupils were dilated with topical phenylephrine (2.5%) and tropicamide (1.0%) followed by application of GenTeal Lubricant Eye Gel, 10 g (Alcon, Ft. Worth, Tex., USA) or 2% methylcellulose to keep the cornea moist and prevent opacification.

Optical Coherence Tomography

The SD-OCT images were obtained using the Bioptigen Spectral-Domain Ophthalmic Imaging System (SD OIS; Bioptigen Envisu R2200; Bioptigen, Inc., Durham, N.C., USA). Imaging included averaged single B-scan and volume intensity scans (VIPs) with images centered on the optic nerve head. Post-imaging analysis was performed by manual assessment of all retinal layers using InVivoVue™ DIVER 2.4 software in a masked fashion (Bioptigen, Inc.).

Electroretinography

To assess rod- and cone-mediated retinal function, full-field electroretinograms (ERGs) were performed using the Espion e2 recording system (Diagnosys, Lowell, Mass.) as described previously (see, Thompson D A, et al., Arch Ophthalmol. 2012; 130(6):712-9). After overnight dark-adaptation, mice were anesthetized and body temperature was maintained at 37° C. with a heating pad. Following pupil dilation, corneal ERGs were recorded from both eyes using gold wire loops mounted in a contact lens electrode (Mayo Corporation, Japan). A gold wire loop placed in the mouth was used as reference, and the ground electrode was placed on the tail. The dark-adapted ERGs were recorded at three intensities: −5.8 log cd·s·m−2 to record the scotopic threshold response, −2.31 log cd·s·m−2 to record the rod isolated response and +1.09 log cd·s·m−2 to record the combined rod-cone response. Ten to 25 responses were recorded at 3 to 60 s depending upon the stimulus intensity. After 10 minutes of light adaptation to a white 32 cd.m−2 rod-suppressing background, light adapted ERGs were recorded at 1.09 log cd·s·m−2. The b-wave amplitude of the averaged response was measured from baseline to the positive peak of the waveform.

Cell Death Assays

Apoptosis was measured by Cell DNA Fragmentation ELISA (Roche Diagnostics) according to the manufacturer's instructions and as previously described (see, Losiewicz M K, Fort P E Invest Ophthalmol Vis Sci. 2011; 52(9):5034-42). Briefly, after homogenizing the retinal tissue or cells in lysis buffer, samples were incubated and spun. 20 μl of the supernatant, as well as of the positive and negative controls were then transferred into the ELISA plate along with the immunoreagent complex. Following incubation and washes, the colorimetric solution was added and incubated until the colorimetric reaction developed. After adding the stop solution, the colorimetric signal was measured with a fluorescence plate reader (SpectraMax Gemini EM; Molecular Devices) with excitation at 405 and 490 nm.

Cell death was also measured by terminal transferase dUTP nick end labeling (TUNEL) with horseradish peroxidase detection in whole-mount retinas as described previously [3]. TUNEL-positive cell counts were calculated as percentages of total cell number at 20× magnification using a light microscope (Leica, Wetzlar, Germany).

Caspase-3/7 activity was measured using the ApoONE Assay (Promega, Madison, Wis.) as described previously (see, Abcouwer S F, Lin C M, Wolpert E B, Shanmugam S, Schaefer E W, Freeman W M, et al. Vascular Permeability and Apoptosis are Separable Processes in Retinal Ischemia-Reperfusion Injury: Effects of Ischemic Preconditioning, Bevacizumab and Etanercept. Invest Ophthalmol Vis Sci. Epub 2010/06/18).

Immunoblot Analysis

Retinas were homogenized by sonication in immunoprecipitation buffer (ip buffer) as previously described (see, Reiter C E, et al., Diabetes. 2006; 55(4):1148-56). Protein concentrations were measured with the Pierce BCA reagent, and all samples were adjusted for equal protein concentration. Retinal lysates were used for immunoblot analysis using the following antibodies: alphaA-crystallin (Santa Cruz), alphaB-crystallin (Enzo life Sciences) and Bax (Cell Signaling). Immunoblots were performed as previously described (see, Wu X, et al., J Biol Chem. 2004; 279(10): 9167-75) but using NuPage gels 4-12% and MES buffer following the manufacturer's instructions. Results were normalized by reprobing the same membrane with an antibody against β-actin (Millipore).

Translocation Analysis

For mitochondrial translocation analysis, retinas were sonicated in a cytosolic buffer that contained 1× phosphate buffered saline (PBS), 300 μM Sucrose, 5 mM PMSF and protease inhibitor cocktail. After centrifugation the supernatant containing the cytosolic fraction was denatured in SDS buffer. The pellet containing the mitochondrial fraction was sonicated in mitochondrial buffer that contained 1×PBS, 1% Triton X-100 (Sigma), 150 mM sodium chloride (NaCl) and protease inhibitor cocktail. After centrifugation the supernatant containing the mitochondrial protein fraction was denatured in SDS buffer and the samples were then analyzed by immunoblot as described above. The purity of each subcellular fraction was confirmed using primary antibodies against α-tubulin and COXIV (Cell Signaling).

Cell Culture and Transfection

R28 retinal neuronal cells were grown in DMEM containing 5 mM glucose supplemented with 10% fetal bovine serum (FBS; Flow Laboratories, Rockville, Md.) and differentiated to neurons on laminin-coated plates with addition of cell-permeable cAMP (Sigma) as described previously (see, Abcouwer S F, Lin C M, Wolpert E B, Shanmugam S, Schaefer E W, Freeman W M, et al. Vascular Permeability and Apoptosis are Separable Processes in Retinal Ischemia- Reperfusion Injury: Effects of Ischemic Preconditioning, Bevacizumab and Etanercept. Invest Ophthalmol Vis Sci. Epub 2010/06/18). Cells were transfected using the Neon™ Transfection System (Invitrogen, Carslbad, Calif.) following the manufacturer's instruction. Briefly, cells were trypsinized and washed in PBS before being resuspended in 100 µl resuspension buffer and electroporated. Cells were then plated in 96-well plate for DNA fragmentation and Caspase assay, or coverslips for TUNEL staining. 36 h after transfection cells were placed in Serum-free DMEM 4 hours before analysis. Serum deprivation of R28 retinal neuronal cells was used as a model of metabolic stress-induced cell death for which the assays were performed as aforementioned.

Co-Immunoprecipitation (IP)

For IP, protein-G sepharose beads (GE Health Care, Piscataway, N.J.) were incubated for 2 hours at 4° C. with a selected mouse monoclonal antibody targeting αA-crystallin (Santa Cruz), or Bax (Cell Signaling). After three washes, 200 µg of total cell lysates, prepared in IP buffer were added and incubated overnight at 4° C. The immune complex was then collected by centrifugation at 1500 g and washed three times with ice cold IP buffer. Immunoblots were then performed as described above. The same blot was reprobed with the immunoprecipitating antibody to account for potential loading differences.

Immunohistochemistry

Immunohistochemical labeling was carried out using the indirect immunofluorescence method. After being fixed for an hour in 4% paraformaldehyde the eyecups were isolated by dissecting out the cornea and lens. The eyecups underwent incubation in increasing concentration of sucrose solution up to 20% before being embedded in a 2:1 ratio of 20% Sucrose:OCT (optimum compound tech) and snap-frozen on dry ice. Sections (10 µm thick) at the level of the optic nerve were then obtained from each experimental group (diabetic and non-diabetic) and mounted onto the same slide. Following permeabilization in a PBS solution containing 0.1% Triton X-100 for 15 minutes, the sections were incubated in a blocking solution of 1% BSA, 0.25% Triton X-100 before incubations with the primary antibodies at 4° C. overnight. Double labeling was done using antibodies against alphaA-crystallin or alphaB-crystallin (Enzo life Sciences) along with anti-glutamine synthetase (Neomarker) or anti-neurofilament H (Covance). Primary antibodies were detected using secondary goat anti-mouse IgG and anti-rabbit IgG antibody coupled to Alexa fluorophore 488 and 594 (Jackson Immunoresearch). Cell nuclei were counterstained using Hoescht, 1:1000 in PBS. Controls were prepared by omitting the primary antibody during the incubation; in these controls, no specific staining could be detected.

Mass Spectrometry Analysis

For immunoprecipitation (IP), protein-G sepharose beads (GE Healthcare) were incubated for 2 h at 4° C. with a selected mouse monoclonal antibody targeting αA-crystallin (Santa Cruz) or αB-crystallin (Abcam). After 3 washes, 400 µg of total retinal lysates (prepared as for immunoblotting) were added and incubated overnight at 4° C. The immune complex was then collected by centrifugation at 1500×g and washed 3 times with ice-cold ip buffer. One set of IP was used to perform immunoblots to check the efficiency of the immunoprecipitation and line-up with a second SDS-PAGE gel fixed and stained using Syproruby (Molecular Probes) according to the manufacturer's instructions. The 3 major bands identified by western blots were matched on the stained gel and excised under UV light.

In-gel digestion was carried out according to standard methods (see, Shevchenko A, et al., Nature protocols. 2006; 1(6):2856-60). Briefly, gel bands were excised and diced into 1 mm$^2$ pieces and placed in Eppendorf tubes. Gel pieces were dehydrated with 100 µL of 50% acetonitrile in 50 mM ammonium bicarbonate buffer (pH=8.0). After removing the liquid, this step was repeated before adding 50 µL DTT in 50 mM ammonium bicarbonate. Samples were incubated for 1 h at 65° C. Liquid was removed and 50 µL of 55 mM chloroacetamide was added. Samples were incubated at room temperature for 45 min in the dark. Gel pieces were washed twice with 100 µL 50% acetonitrile in 50 mM ammonium bicarbonate and then dried in a speed vac. Trypsin (30 µL of 10 ng/µL; Thermo Scientific Pierce) was added and gel pieces were rehydrated for 30 min on ice. After rehydration, an additional 30 µL aliquot of ammonium bicarbonate was added and samples were incubated overnight at 37° C. with shaking. Two volume of acetonitrile, 50% in 0.5% formic acid, was added to each tube and samples were incubated at 37° C. for 15 min. The supernatant was collected, dried in a speed vac, and stored at −20° C. until analysis.

Dried samples were dissolved in 10 µL of 0.1% formic acid containing 4 HRT reference peptides and 3 µL were injected onto a custom packed 5 cm C18 trapping column (Phenomenex, Luna 5 µm, 300 angstrom) and then resolved using a C18 (Phenomonex Luna 3 µm, 300 angstrom) capillary column 100 µm i.d.×25 cm). A nanoAquity (Waters) HLPC was used to gradient elute peptides into a triple quadrupole mass spectrometer (Thermo Scientific Vantage). After 5 min loading onto the trapping column at 3 µl/min (99% A—water 0.1% formic acid, 1% B—acetonitrile 0.1% formic acid), the following gradient used to resolve peptides at 400 nl/minute: 1% B to 45% B at 60 minutes, to 90% B at 75 minutes for 5 minutes, return to 1% B at 85 min, and remain there for the final 10 minutes. Because of the number of transitions to be monitored, 2 multiple reaction monitoring (MRM) experiments (49 transitions in the first and 56 in the second) were used to detect peptides (see Table 2) throughout the course of the gradient elution. Specific transitions were chosen based on pilot non-targeted LC-MS/MS analysis of α-crystallin tryptic digests performed on a Velos linear ion trap instrument (Thermo Scientific). A precursor ion window of 0.2 m/z and a scan time of 50 msec were used. Predicted collision energy values, data analysis, and overall peptide quantification were accomplished using Skyline (see, MacLean B, et al., Bioinformatics. 2010; 26(7): 966-8).

TABLE 2

MRM Transitions for LC-MS/MS Measurement of Peptide Abundances

| Peptide | Sequence | Precursor m/z | Transitions (ion, m/z) |
|---|---|---|---|
| αA 145-156 | VQSGLDAGHSER | 628.30$^{++}$ | y5, 585.27 |
| | | | y6, 656.31 |
| | | | y7, 771.34 |
| | | | y9, 941.44 |
| | | | y10, 1028.48 |
| αA 145-156 phos. | VQpSGLDAGHSER | 668.29$^{++}$ | y5, 585.27 |
| | | | y6, 656.31 |
| | | | y7, 771.34 |
| | | | y9, 941.44 |
| | | | y10, 1010.47$^a$ |

$^a$y10 ion monitored as [m-98]$^+$ ion

Statistical Analysis

For all immunoblot experiments, the data were normalized to the β-actin signal as control before analysis. ANOVA models with heterogeneous variances, adjusted for the replication of the experiment, were fit to the data to assess differences between diabetic and control mice. The means±SEM and statistically significant differences are reported. Analyses were performed using non-repeated measures ANOVA followed by the SNK test for multiple comparisons or t-test for a single comparison.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A composition comprising an αA-crystallin protein modulating compound, including pharmaceutically acceptable salts, solvates, and/or prodrugs thereof; wherein the αA-crystallin protein modulating compound is configured to mimic a phosphorylated wild type αA-crystallin protein, wherein said αA-crystallin protein modulating compound comprises a sequence of SEQ ID 1 having a threonine (T) to aspartic acid (D) or glutamate (E) substitution at amino acid position 148 or comprises a sequence of SEQ ID 2 with a serine (S) to aspartic acid (D) or glutamate (E) substitution at amino acid position 148.

2. A kit comprising a compound of claim 1 and instructions for administering said compound to a patient having or at risk for having diabetic retinopathy.

* * * * *

SEQUENCE LISTING

```
<160> NUMBER OF SEQ ID NOS: 4

<210> SEQ ID NO 1
<211> LENGTH: 173
<212> TYPE: PRT
<213> ORGANISM: Homo sapiens

<400> SEQUENCE: 1

Met Asp Val Thr Ile Gln His Pro Trp Phe Lys Arg Thr Leu Gly Pro
1               5                   10                  15

Phe Tyr Pro Ser Arg Leu Phe Asp Gln Phe Phe Gly Glu Gly Leu Phe
                20                  25                  30

Glu Tyr Asp Leu Leu Pro Phe Leu Ser Ser Thr Ile Ser Pro Tyr Tyr
            35                  40                  45

Arg Gln Ser Leu Phe Arg Thr Val Leu Asp Ser Gly Ile Ser Glu Val
        50                  55                  60

Arg Ser Asp Arg Asp Lys Phe Val Ile Phe Leu Asp Val Lys His Phe
65                  70                  75                  80

Ser Pro Glu Asp Leu Thr Val Lys Val Gln Asp Asp Phe Val Glu Ile
                85                  90                  95

His Gly Lys His Asn Glu Arg Gln Asp Asp His Gly Tyr Ile Ser Arg
            100                 105                 110

Glu Phe His Arg Arg Tyr Arg Leu Pro Ser Asn Val Asp Gln Ser Ala
        115                 120                 125

Leu Ser Cys Ser Leu Ser Ala Asp Gly Met Leu Thr Phe Cys Gly Pro
    130                 135                 140

Lys Ile Gln Thr Gly Leu Asp Ala Thr His Ala Glu Arg Ala Ile Pro
145                 150                 155                 160

Val Ser Arg Glu Glu Lys Pro Thr Ser Ala Pro Ser Ser
                165                 170

<210> SEQ ID NO 2
<211> LENGTH: 173
<212> TYPE: PRT
<213> ORGANISM: Murine

<400> SEQUENCE: 2

Met Asp Val Thr Ile Gln His Pro Trp Phe Lys Arg Ala Leu Gly Pro
1               5                   10                  15

Phe Tyr Pro Ser Arg Leu Phe Asp Gln Phe Phe Gly Glu Gly Leu Phe
                20                  25                  30
```

Glu Tyr Asp Leu Leu Pro Phe Leu Ser Ser Thr Ile Ser Pro Tyr Tyr
            35                  40                  45

Arg Gln Ser Leu Phe Arg Thr Val Leu Asp Ser Gly Ile Ser Glu Val
 50                  55                  60

Arg Ser Asp Arg Asp Lys Phe Val Ile Phe Leu Asp Val Lys His Phe
 65                  70                  75                  80

Ser Pro Glu Asp Leu Thr Val Lys Val Leu Glu Asp Phe Val Glu Ile
                 85                  90                  95

His Gly Lys His Asn Glu Arg Gln Asp Asp His Gly Tyr Ile Ser Arg
                100                 105                 110

Glu Phe His Arg Arg Tyr Arg Leu Pro Ser Asn Val Asp Gln Ser Ala
                115                 120                 125

Leu Ser Cys Ser Leu Ser Ala Asp Gly Met Leu Thr Phe Ser Gly Pro
                130                 135                 140

Lys Val Gln Ser Gly Leu Asp Ala Gly His Ser Glu Arg Ala Ile Pro
145                 150                 155                 160

Val Ser Arg Glu Glu Lys Pro Ser Ser Ala Pro Ser Ser
                165                 170

<210> SEQ ID NO 3
<211> LENGTH: 173
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: Xaa = D or E

<400> SEQUENCE: 3

Met Asp Val Thr Ile Gln His Pro Trp Phe Lys Arg Thr Leu Gly Pro
 1               5                  10                  15

Phe Tyr Pro Ser Arg Leu Phe Asp Gln Phe Phe Gly Glu Gly Leu Phe
                 20                  25                  30

Glu Tyr Asp Leu Leu Pro Phe Leu Ser Ser Thr Ile Ser Pro Tyr Tyr
            35                  40                  45

Arg Gln Ser Leu Phe Arg Thr Val Leu Asp Ser Gly Ile Ser Glu Val
 50                  55                  60

Arg Ser Asp Arg Asp Lys Phe Val Ile Phe Leu Asp Val Lys His Phe
 65                  70                  75                  80

Ser Pro Glu Asp Leu Thr Val Lys Val Gln Asp Asp Phe Val Glu Ile
                 85                  90                  95

His Gly Lys His Asn Glu Arg Gln Asp Asp His Gly Tyr Ile Ser Arg
                100                 105                 110

Glu Phe His Arg Arg Tyr Arg Leu Pro Ser Asn Val Asp Gln Ser Ala
                115                 120                 125

Leu Ser Cys Ser Leu Ser Ala Asp Gly Met Leu Thr Phe Cys Gly Pro
                130                 135                 140

Lys Ile Gln Xaa Gly Leu Asp Ala Thr His Ala Glu Arg Ala Ile Pro
145                 150                 155                 160

Val Ser Arg Glu Glu Lys Pro Thr Ser Ala Pro Ser Ser
                165                 170

<210> SEQ ID NO 4
<211> LENGTH: 173
<212> TYPE: PRT
<213> ORGANISM: Artificial sequence
<220> FEATURE:

<223> OTHER INFORMATION: Synthetic peptide
<220> FEATURE:
<221> NAME/KEY: misc_feature
<223> OTHER INFORMATION: Xaa = D or E

<400> SEQUENCE: 4

```
Met Asp Val Thr Ile Gln His Pro Trp Phe Lys Arg Ala Leu Gly Pro
1               5                   10                  15

Phe Tyr Pro Ser Arg Leu Phe Asp Gln Phe Phe Gly Glu Gly Leu Phe
            20                  25                  30

Glu Tyr Asp Leu Leu Pro Phe Leu Ser Ser Thr Ile Ser Pro Tyr Tyr
        35                  40                  45

Arg Gln Ser Leu Phe Arg Thr Val Leu Asp Ser Gly Ile Ser Glu Val
    50                  55                  60

Arg Ser Asp Arg Asp Lys Phe Val Ile Phe Leu Asp Val Lys His Phe
65                  70                  75                  80

Ser Pro Glu Asp Leu Thr Val Lys Val Leu Glu Asp Phe Val Glu Ile
            85                  90                  95

His Gly Lys His Asn Glu Arg Gln Asp Asp His Gly Tyr Ile Ser Arg
                100                 105                 110

Glu Phe His Arg Arg Tyr Arg Leu Pro Ser Asn Val Asp Gln Ser Ala
            115                 120                 125

Leu Ser Cys Ser Leu Ser Ala Asp Gly Met Leu Thr Phe Ser Gly Pro
        130                 135                 140

Lys Val Gln Xaa Gly Leu Asp Ala Gly His Ser Glu Arg Ala Ile Pro
145                 150                 155                 160

Val Ser Arg Glu Glu Lys Pro Ser Ser Ala Pro Ser Ser
                165                 170
```